US012742791B2

(12) United States Patent
Suzuki et al.

(10) Patent No.: US 12,742,791 B2

(45) Date of Patent: Sep. 22, 2026

(54) METHOD, ANALYSIS SYSTEM, ANALYZER, AND COMPUTER PROGRAM FOR ANALYZING CAUSE OF PROLONGING COAGULATION TIME

(71) Applicants: NIIGATA UNIVERSITY, Niigata (JP); SYSMEX CORPORATION, Kobe (JP)

(72) Inventors: Takeshi Suzuki, Kobe (JP); Masato Matsuda, Niigata (JP); Masato Moriyama, Niigata (JP); Sho Shinohara, Kobe (JP); Keisuke Kitano, Kobe (JP); Tsukasa Suetake, Kobe (JP); Yutaka Komiyama, Osaka (JP)

(73) Assignees: NIIGATA UNIVERSITY, Niigata (JP); SYSMEX CORPORATION, Hyogo (JP)

( * ) Notice: Subject to any disclaimer, the term of this patent is extended or adjusted under 35 U.S.C. 154(b) by 1030 days.

(21) Appl. No.: 17/955,129

(22) Filed: Sep. 28, 2022

(65) Prior Publication Data

US 2023/0098487 A1 Mar. 30, 2023

(30) Foreign Application Priority Data

Sep. 30, 2021 (JP) ................................ 2021-161543

(51) Int. Cl.
*G01N 33/86* (2006.01)

(52) U.S. Cl.
CPC .................................... *G01N 33/86* (2013.01)

(58) Field of Classification Search
CPC .... G01N 33/86; G01N 33/49; G01N 33/4905; G01N 2400/40; Y10T 436/11

(Continued)

(56) References Cited

U.S. PATENT DOCUMENTS 10,048,249 B2 8/2018 Nishimura et al.
2011/0129862 A1* 6/2011 Nakamura ............. G01N 33/86 435/13
2014/0255254 A1* 9/2014 Yamaguchi ........ G01N 33/4905 422/73
2016/0178651 A1* 6/2016 Shima ................ G01N 33/4905 435/13

(Continued)

FOREIGN PATENT DOCUMENTS

WO 2016/136558 A1 9/2016

OTHER PUBLICATIONS

European Patent Office Communication pursuant to Article 94(3) EPC regarding Application No. 22 196 799.5 dated Nov. 6, 2023, 8 pages.

(Continued)

*Primary Examiner* — Maureen Wallenhorst

(74) *Attorney, Agent, or Firm* — Crowell & Moring LLP

(57) ABSTRACT

A method for analyzing a cause of prolonging coagulation time of a blood specimen includes: adding a calcium solution to a first sample resulting from a first waiting time from mixing of a blood specimen from a subject and a measurement reagent for an activated partial thromboplastin time; obtaining a first coagulation time and/or a first parameter regarding a differential of a coagulation waveform, for the first sample; adding the calcium solution to a second sample resulting from a second waiting time, which is longer than the first waiting time, from mixing of the blood specimen from the subject and the measurement reagent; obtaining a second coagulation time and/or a second parameter regarding a differential of a coagulation waveform, for the second sample; and obtaining information regarding a cause of prolonging a coagulation time, on the basis of the first and second coagulation time and/or the first and second parameter.

11 Claims, 20 Drawing Sheets

(58) Field of Classification Search
USPC ............ 436/63, 69, 43, 164; 422/73, 82.05, 422/82.09
See application file for complete search history.

(56) References Cited

U.S. PATENT DOCUMENTS

| | | | | |
|---|---|---|---|---|
| 2016/0291042 | A1* | 10/2016 | Kumano | G01N 21/77 |
| 2017/0350907 | A1* | 12/2017 | Ieko | G01N 35/025 |
| 2018/0356433 | A1* | 12/2018 | Kumano | G01N 33/96 |

OTHER PUBLICATIONS

M. Ieko et al., "Cross-Mixing Test to Detect Lupus Anticoagulant for Diagnosis of Antiphospholipid Syndrome", The Official Journal of Japanese Society of Laboratory Medicine, Oct. 2009, pp. 990-998, vol. 57, No. 10, Japanese Society of Laboratory Medicine, Japan.
Detailed explanation of "Cross-mixing test", Glossary from Website of The Japanese Society on Thrombosis and Hemostasis at least as early as 2021.
Extended European Search Report, dated Feb. 23, 2023, pp. 1-8, issued in European Application No. 22196799.5, European Patent Office, Munich, Germany.
Stefano Barco et al.: "Severe plasma prekallikrein deficiency: Clinical characteristics, novel KLKB1 mutations, and estimated prevalance", Journal of Thrombosis And Haemostasis, vol. 18, No. 7, at least as early as Jul. 1, 2020, pp. 1598-1617, ScienceDirect available at URL https://www.sciencedirect.com/science/article/pii/S153878362201323X.

* cited by examiner

< CONTROLLER 24 >
MEASUREMENT PROCESS
S101
READ OUT INFORMATION REGARDING FIRST AND SECOND WAITING TIMES
S102
PREPARE FIRST SAMPLE AND ADD CALCIUM SOLUTION
S103
OBTAIN MEASUREMENT DATA OF FIRST SAMPLE
S104
PREPARE SECOND SAMPLE AND ADD CALCIUM SOLUTION
S105
OBTAIN MEASUREMENT DATA OF SECOND SAMPLE
TO STEP S15

| 3000 | 3000 | 3000 | . . . | 3000 | 2990 | . . . | 1010 | 1000 | . . . | 1000 |
|---|---|---|---|---|---|---|---|---|---|---|
| 0.0 | 0.1 | 0.2 | . . . | xx | xx | . . . | xx | xx | . . . | 180.0 |

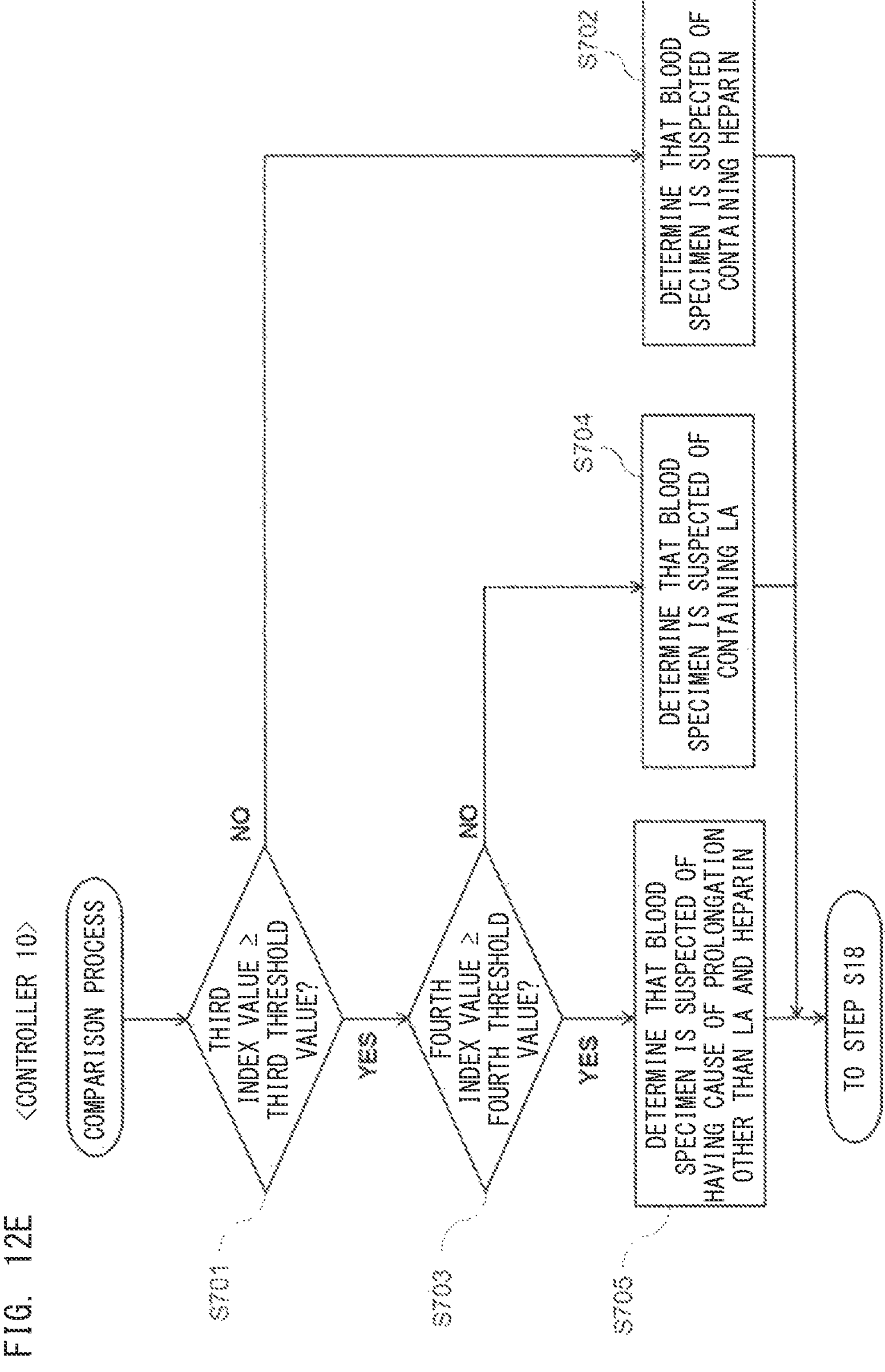
FIG. 12E
<CONTROLLER 10>
COMPARISON PROCESS
S701
THIRD INDEX VALUE ≥ THIRD THRESHOLD VALUE?
YES
NO
S702
DETERMINE THAT BLOOD SPECIMEN IS SUSPECTED OF CONTAINING HEPARIN
S703
FOURTH INDEX VALUE ≥ FOURTH THRESHOLD VALUE?
YES
NO
S704
DETERMINE THAT BLOOD SPECIMEN IS SUSPECTED OF CONTAINING LA
S705
DETERMINE THAT BLOOD SPECIMEN IS SUSPECTED OF HAVING CAUSE OF PROLONGATION OTHER THAN LA AND HEPARIN
TO STEP S18

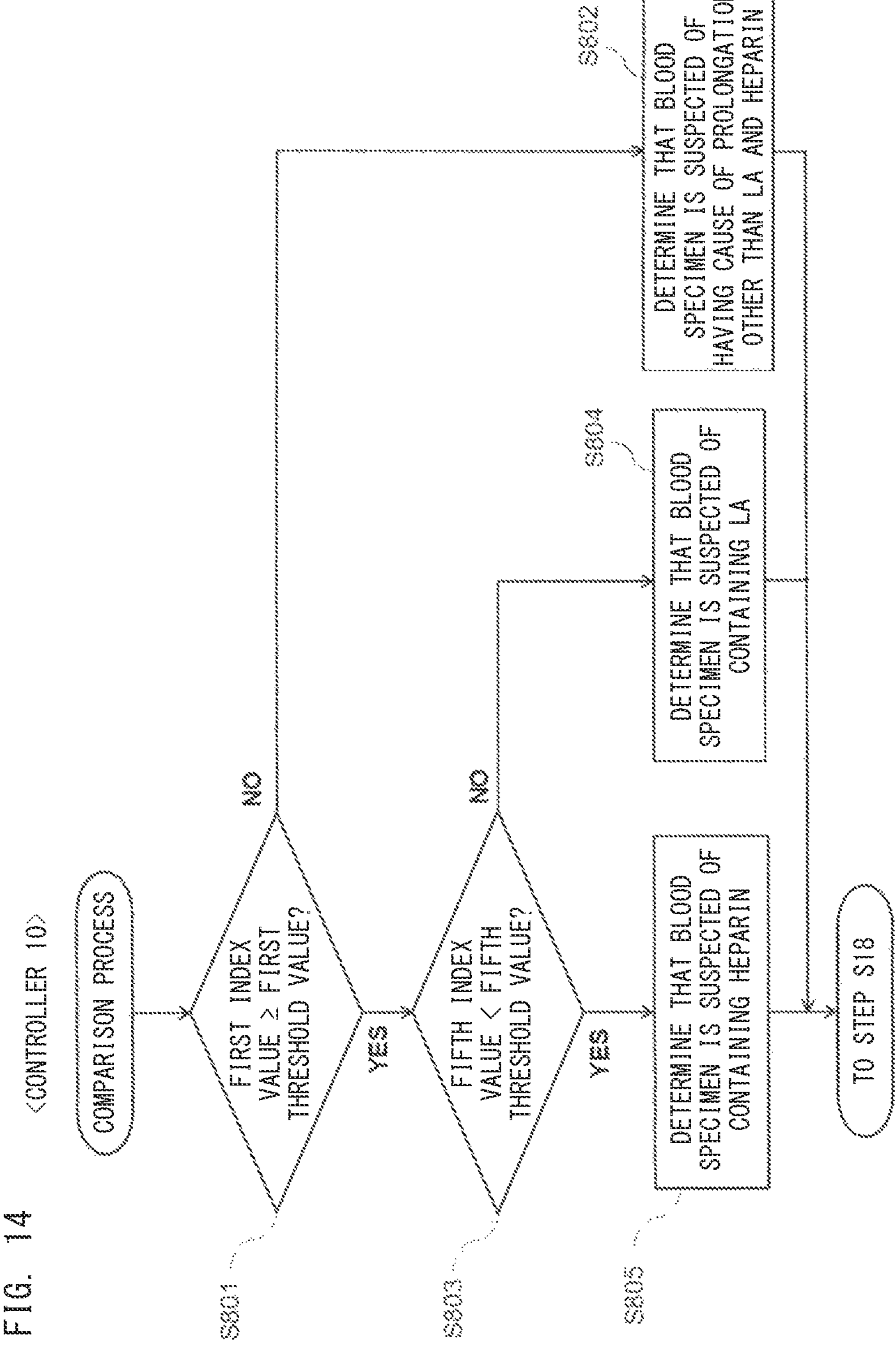
FIG. 14
〈CONTROLLER 10〉
COMPARISON PROCESS
S801
FIRST INDEX VALUE ≥ FIRST THRESHOLD VALUE?
YES
NO
S802
DETERMINE THAT BLOOD SPECIMEN IS SUSPECTED OF HAVING CAUSE OF PROLONGATION OTHER THAN LA AND HEPARIN
S803
FIFTH INDEX VALUE < FIFTH THRESHOLD VALUE?
YES
NO
S804
DETERMINE THAT BLOOD SPECIMEN IS SUSPECTED OF CONTAINING LA
S805
DETERMINE THAT BLOOD SPECIMEN IS SUSPECTED OF CONTAINING HEPARIN
TO STEP S18

INDEX VALUE
(THIRD APTT/FOURTH APTT)
HEALTHY
LA
COAGULATION FACTOR DEFICIENCY
HEPARIN
WARFARIN
DOAC

METHOD, ANALYSIS SYSTEM, ANALYZER, AND COMPUTER PROGRAM FOR ANALYZING CAUSE OF PROLONGING COAGULATION TIME

RELATED APPLICATIONS

This application claims priority to prior Japanese Patent Application No. 2021-161543, filed on Sep. 30, 2021, entitled "METHOD, ANALYSIS SYSTEM, ANALYZER, AND COMPUTER PROGRAM FOR ANALYZING CAUSE OF PROLONGING COAGULATION TIME", the entire content of which is incorporated herein by reference.

BACKGROUND OF THE INVENTION

The present invention relates to a method for analyzing a cause of prolonging a coagulation time of a blood specimen. The present invention relates to a system for analyzing a cause of prolonging a coagulation time of a blood specimen. The present invention relates to an analyzer for analyzing a cause of prolonging a coagulation time of a blood specimen. The present invention relates to a computer program for analyzing a cause of prolonging a coagulation time of a blood specimen.

It is known that, if a coagulation time is found to have been prolonged in a blood coagulation test, a cause of the prolongation is analyzed in a cross-mixing test. In a cross-mixing test, a plurality of plasmas (mixed plasmas) are prepared by mixing a plasma from a subject (subject plasma) and a plasma from a healthy individual (normal plasma) such that the mixing ratio between the subject plasma and the normal plasma varies among the mixed plasmas, coagulation times of the plurality of respective mixed plasmas are measured, and a cause of prolonging a coagulation time is analyzed from a graph having a vertical axis indicating coagulation time and a horizontal axis indicating mixing ratio. In addition, a method in International Publication WO2016/136558 is known as a method for quantitatively analyzing a cause of prolonging a coagulation time, on the basis of a graph obtained through a cross-mixing test. International Publication WO2016/136558 discloses a method for analyzing a cause of prolonging a coagulation time by using a result of performing arithmetic operation with: a first quantification index obtained from coagulation times of a subject plasma, a normal plasma, and a mixed plasma that have been measured by using a blood coagulation measurement device without incubating these plasmas in advance; and a second quantification index obtained from coagulation times of the subject plasma, the normal plasma, and the mixed plasma that have been measured by using the blood coagulation measurement device after incubating these plasmas under a predetermined condition (at 37° C. for two hours).

The cross-mixing test and the method in the above International Publication WO2016/136558 necessitates usage of mixed plasmas obtained by mixing a subject plasma and a normal plasma. However, preparation of a mixed plasma necessitates preparation of a normal plasma and mixing of the prepared normal plasma and a subject plasma, resulting in complicated work.

SUMMARY OF THE INVENTION

The scope of the present invention is defined solely by the appended claims, and is not affected to any degree by the statements within this summary.

The present invention provides a method for analyzing a cause of prolonging a coagulation time of a blood specimen. The method includes: adding a calcium solution to a first sample resulting from an elapse of a first waiting time from mixing of a blood specimen from a subject and a measurement reagent for an activated partial thromboplastin time (APTT); obtaining a first coagulation time and/or a first parameter regarding a differential of a coagulation waveform, for the first sample to which the calcium solution has been added; adding the calcium solution to a second sample resulting from an elapse of a second waiting time, which is longer than the first waiting time, from mixing of the blood specimen from the subject and the APTT measurement reagent; obtaining a second coagulation time and/or a second parameter regarding a differential of a coagulation waveform, for the second sample to which the calcium solution has been added; and obtaining information regarding a cause of prolonging a coagulation time, on the basis of the first coagulation time and/or the first parameter and the second coagulation time and/or the second parameter.

The present invention provides an analysis system including: a sample preparation part; a light applicator; a detector; and a controller. The controller is programmed to control the sample preparation part to add a calcium solution to a first sample resulting from an elapse of a first waiting time from mixing of a blood specimen from a subject and an APTT measurement reagent and add the calcium solution to a second sample resulting from an elapse of a second waiting time, which is longer than the first waiting time, from mixing of the blood specimen from the subject and the APTT measurement reagent. The controller is programmed to control the light applicator to apply light to the first sample and the second sample to each of which the calcium solution has been added. The controller is programmed to receive each output from the detector having detected the light having passed through the first sample and the second sample. The controller is programmed to obtain, on the basis of the output from the detector, a first coagulation time and/or a first parameter regarding a differential of a coagulation waveform, for the first sample to which the calcium solution has been added, and a second coagulation time and/or a second parameter regarding a differential of a coagulation waveform, for the second sample to which the calcium solution has been added. The controller is programmed to output information regarding a cause of prolonging a coagulation time, on the basis of the first coagulation time and/or the first parameter and the second coagulation time and/or the second parameter.

The present invention provides an analyzer configured to analyze a cause of prolonging a coagulation time of a blood specimen. The analyzer includes a controller. The controller is programmed to: obtain a first coagulation time and/or a first parameter regarding a differential of a coagulation waveform, for a first sample to which a calcium solution has been added; obtain a second coagulation time and/or a second parameter regarding a differential of a coagulation waveform, for a second sample to which the calcium solution has been added; and output information regarding a cause of prolonging a coagulation time, on the basis of the obtained first coagulation time and/or the obtained first parameter and the obtained second coagulation time and/or the obtained second parameter. The adding of the calcium solution to the first sample is performed after a first waiting time has elapsed from mixing of a blood specimen from a subject and an APTT measurement reagent, and the adding of the calcium solution to the second sample is performed after a second waiting time longer than the first waiting time has elapsed from mixing of the blood specimen from the subject and the APTT measurement reagent.

The present invention provides a non-transitory computer-readable medium storing therein a computer program for analyzing a cause of prolonging a coagulation time of a blood specimen. The computer program is configured to cause a computer to execute: obtaining a first coagulation time and/or a first parameter regarding a differential of a coagulation waveform, for a first sample to which a calcium solution has been added; obtaining a second coagulation time and/or a second parameter regarding a differential of a coagulation waveform, for a second sample to which the calcium solution has been added; and outputting information regarding a cause of prolonging a coagulation time, on the basis of the first coagulation time and/or the first parameter and the second coagulation time and/or the second parameter. The adding of the calcium solution to the first sample is performed after a first waiting time has elapsed from mixing of a blood specimen from a subject and an APTT measurement reagent, and the adding of the calcium solution to the second sample is performed after a second waiting time longer than the first waiting time has elapsed from mixing of the blood specimen from the subject and the APTT measurement reagent.

BRIEF DESCRIPTION OF THE DRAWINGS

FIG. 12E is a flowchart showing a comparison process to be performed by the controller 10;

FIG. 14 is a flowchart showing a comparison process to be performed by the controller 10;

DETAILED DESCRIPTION OF THE PREFERRED EMBODIMENTS

1. Analysis System 1000

Figure 1:
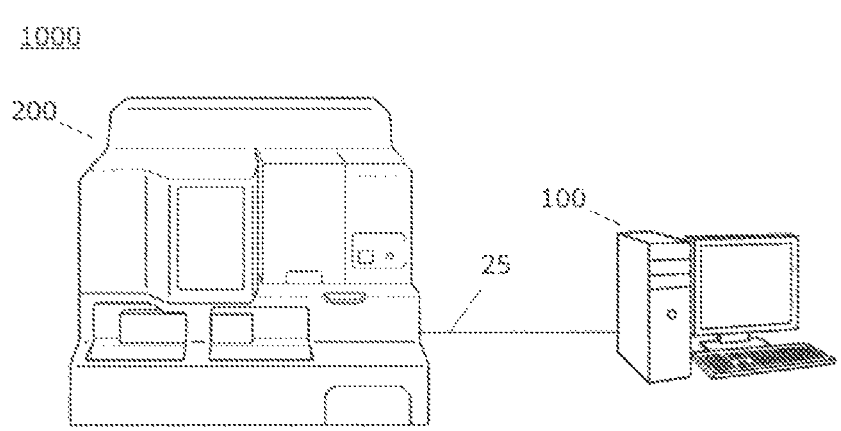
FIG. 1 shows the appearance of an analysis system 1000.

With reference to FIG. 1, an analysis system 1000 includes: an analyzer 100 which analyzes a cause of prolonging a coagulation time of a blood specimen (hereinafter, also referred to as "cause of coagulation time prolongation"); and a measurement device 200 including a detector which obtains optical information through application of light to a blood specimen in which a coagulation reaction has started. The analyzer 100 and the measurement device 200 are connected to each other with a communication cable 25.

Examples of the blood specimen to be analyzed in the analysis system 1000 include whole blood and plasma. A preferable blood specimen is plasma. Anticoagulants other than heparin, warfarin, and a direct oral anticoagulant (DOAC) may be added to the blood specimen at the time of blood collection. As such an anticoagulant, a citrate such as trisodium citrate can be used.

A subject is not particularly limited, and examples of the subject include a subject who has been found to have experienced prolongation of a coagulation time in a coagulation test. The type of the coagulation time found to have been prolonged in the coagulation test is not particularly limited, and examples of the type of the coagulation time include APTT, prothrombin time, thrombin time, and the like. Among these types of coagulation times, APTT is preferable. The cause of coagulation time prolongation is not particularly limited, and examples of the cause include the presence of lupus anticoagulant (LA), coagulation factor deficiency, mixing or administration of heparin, administration of warfarin, administration of a DOAC, and the like.

The DOAC is not particularly limited, and examples of the DOAC include factor Xa inhibitors and thrombin inhibitors. Factor Xa inhibitors are directly bound to factor Xa so as to inhibit conversion of prothrombin into thrombin. Examples of the factor Xa inhibitors include rivaroxaban, apixaban, edoxaban, betrixaban, otamixaban, razaxaban, darexaban, letaxaban, eribaxaban, antistasin, and the like. Thrombin inhibitors are directly bound to thrombin so as to inhibit fibrinogen activation that is mediated by the thrombin. Examples of the thrombin inhibitors include dabigatran, bivalirudin, hirudin, lepirudin, desirudin, argatroban, melagatran, ximelagatran, and the like.

1.1 Analyzer 100

Figure 2:
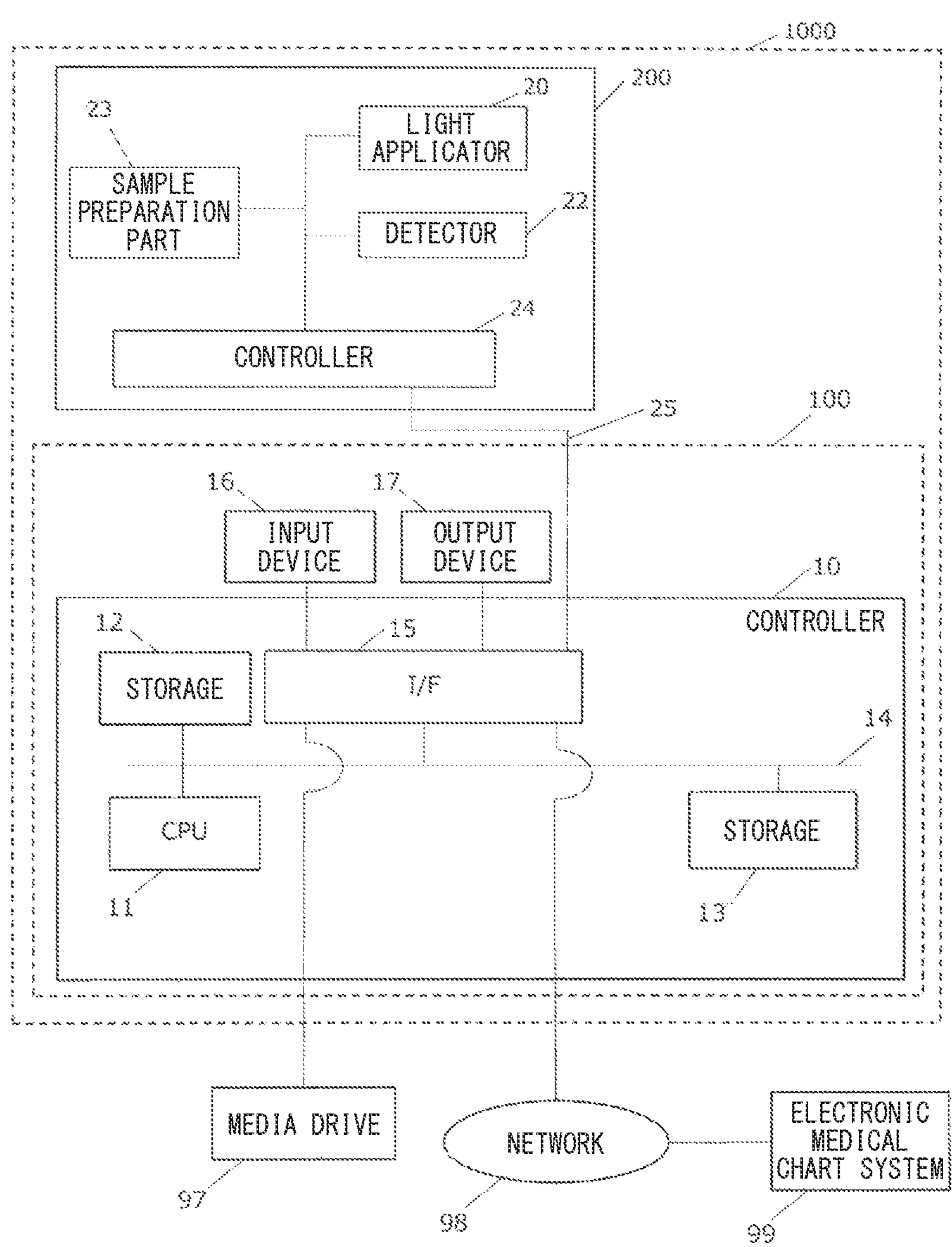
FIG. 2 shows a hardware configuration of the analysis system 1000.

With reference to FIG. 2, the analyzer 100 is communicably connected to the measurement device 200. Further, the analyzer 100 is connected to a media drive 97. Further, the analyzer 100 is connected to an electronic medical chart system 99 via a network 98. The network 98 is, for example, a local area network (LAN). The network 98 may be the Internet.

The analyzer 100 includes a controller 10, an input device 16, and an output device 17. The controller 10 includes: a CPU (central processing unit) 11 which performs data processing; a storage 12 which is used as a work area for data processing; a storage 13 in which information to be transferred to the storage 12 is saved; a bus 14 through which data is transmitted between the devices; and an interface (I/F) 15 through which data is inputted from and outputted to an external device. The input device 16, the output device 17, the media drive 97, the network 98, and the measurement device 200 are connected to the interface 15.

The storage 12 is composed of a DRAM and an SRAM. The storage 13 is a solid-state drive. The storage 13 may be a hard disk drive. The interface 15 is of Ethernet. The interface 15 may be of IEEE1394, USB, or the like. The input device 16 is composed of a keyboard and a mouse. The output device 17 is a liquid crystal display. The output device 17 may be an organic electroluminescence display. Information regarding a cause of coagulation time prolongation is outputted to the output device 17. Further, a coagulation time of a blood specimen from a subject and a parameter regarding a differential of a coagulation waveform may be outputted to the output device 17.

Figure 3:
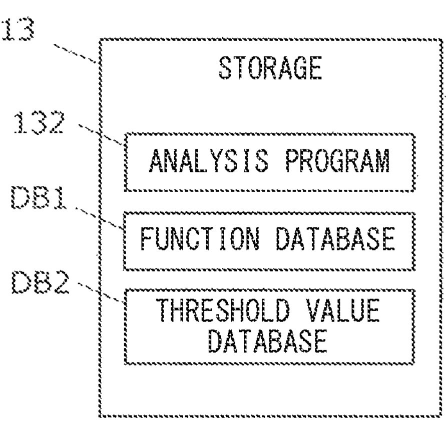
FIG. 3 shows information stored in a storage 13.

With reference to FIG. 3, the storage 13 stores therein: an analysis program 132 for analyzing a cause of coagulation time prolongation; a function database DB1 storing therein mathematical expressions for use in analysis; and a threshold value database DB2 storing therein threshold values.

1.2 Configuration of Measurement Device

With reference to FIG. 2, the measurement device 200 includes a light applicator 20, a detector 22, a sample preparation part 23, and a controller 24.

The controller 24 controls the light applicator 20, the detector 22, and the sample preparation part 23, and performs data communication with the controller 10 of the analyzer 100. The controller 24 includes a CPU, a DRAM, an SRAM, a solid-state drive, and Ethernet in the same manner as the controller 10. The solid-state drive stores therein: a measurement program for causing the measurement device 200 to perform blood coagulation measurement; and waiting times described later.

Figure 4:
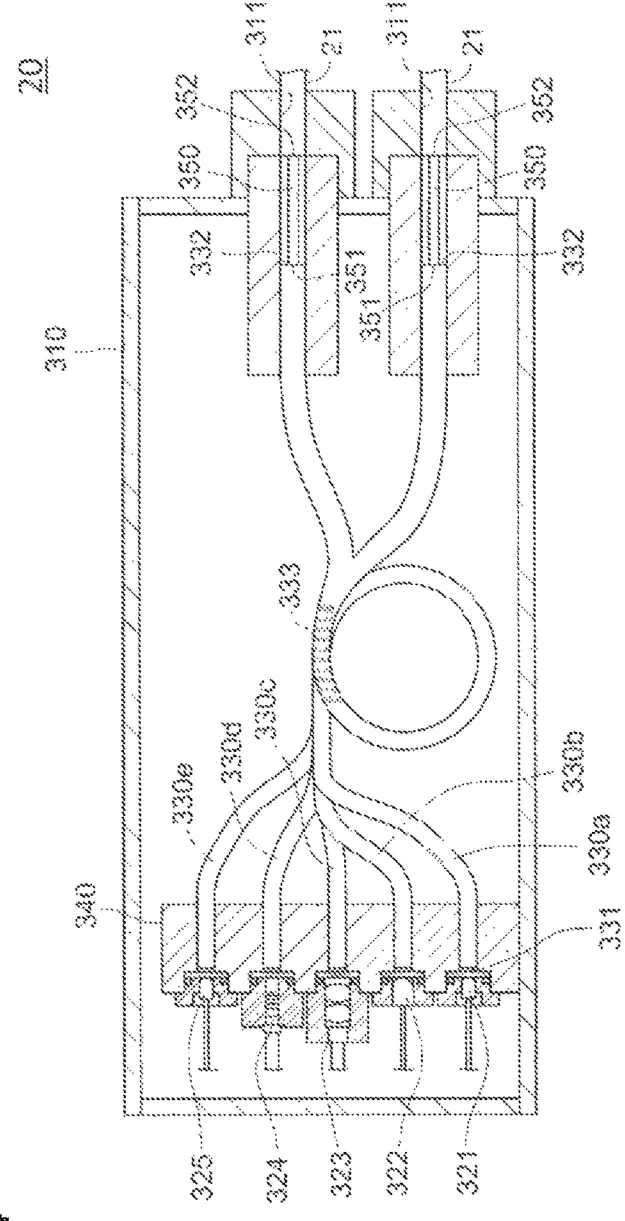
FIG. 4 shows a configuration of a light applicator 20.

With reference to FIG. 4, the light applicator 20 includes: five light sources 321, 322, 323, 324, and 325; five optical fiber parts 330*a*, 330*b*, 330*c*, 330*d*, and 330*e*; and one holding member 340. The optical fiber parts 330*a* to 330*e* are provided so as to correspond to the five light sources 321 to 325, respectively. The holding member 340 holds the light sources 321 to 325 and light entry ends 331 of the optical fiber parts 330*a* to 330*e*. The light sources 321 to 325, the optical fiber parts 330*a* to 330*e*, and the holding member 340 are accommodated in a housing 310 made of metal. Each of the light sources 321 to 325 is implemented by an LED. The first light source 321 generates 660-nm light, the second light source 322 generates 405-nm light, the third light source 323 generates 800-nm light, the fourth light source 324 generates 340-nm light, and the fifth light source 325 generates 575-nm light. The controller 24 controls the light sources 321 to 325 to be turned on and off.

Each of the optical fiber parts 330*a* to 330*e* is formed as a cable obtained by bundling optical fiber element wires each having one core. The optical fiber parts 330*a* to 330*e* are bundled at intermediate portions 333 thereof, to obtain one optical fiber part. The one optical fiber part obtained by bundling the optical fiber parts 330*a* to 330*e* is divided into two bundles, and light outputting ends 332 of the respective bundles are held in outlets 311 provided in the housing 310. Light entry ends 352 of optical fibers 21 are also held in the outlets 311. Each of the optical fibers 21 connects the light applicator 20 and the detector 22 to each other. Light from the light applicator 20 is supplied via the optical fiber 21 to the detector 22. A uniformization member 350 is provided between each of the light outputting ends 332 of the optical fiber parts 330*a* to 330*e* and a corresponding one of the light entry ends 352 of the optical fibers 21. The uniformization member 350 uniformizes an intensity distribution of light outputted from the light outputting end 332. The uniformization member 350 is a member that causes light having entered from a light entry surface 351 to be reflected multiple times inside the uniformization member 350. The uniformization member 350 is a rod homogenizer having the shape of a polygonal prism.

Figure 5A:
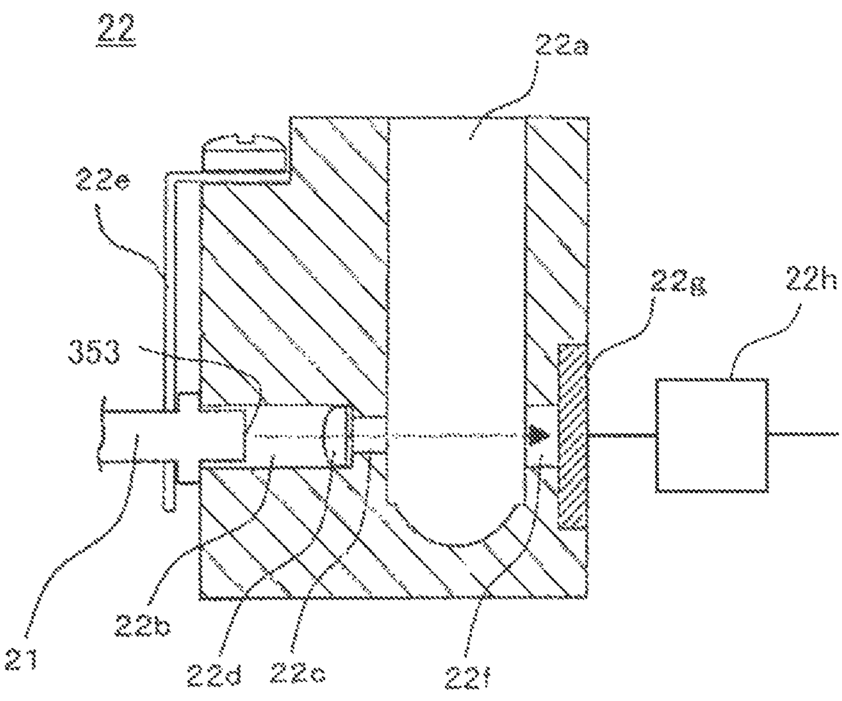
FIG. 5A shows a configuration of a detector 22 in a state of having no cuvette 80.
Figure 5B:
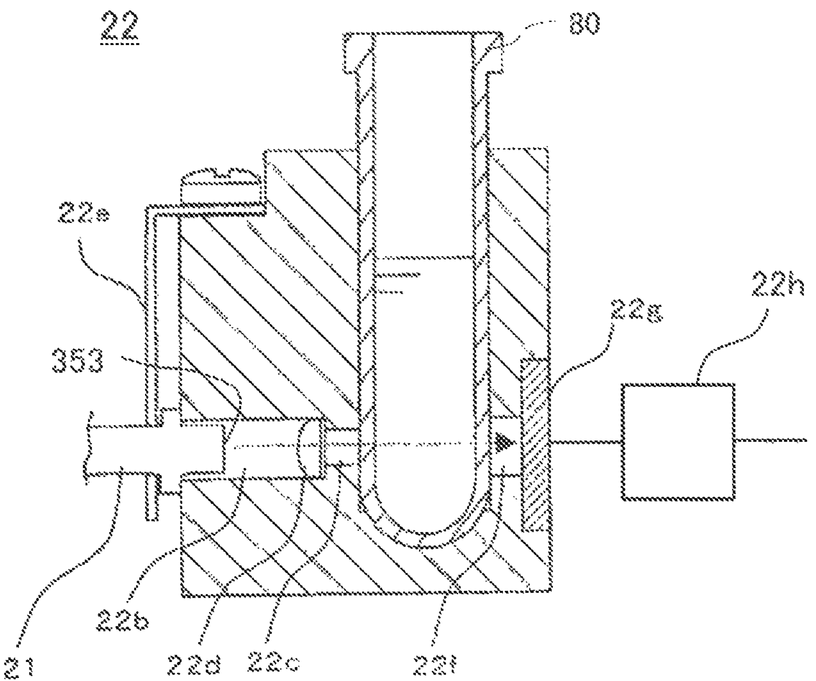
FIG. 5B shows a configuration of the detector 22 in a state of having a cuvette 80.

With reference to FIG. 5A and FIG. 5B, the detector 22 is provided to each of the optical fibers 21 connected to the light applicator 20, and a configuration for connection between the optical fiber 21 and the detector 22 and a hardware configuration of the detector 22 are the same among all the detectors 22. Therefore, one of the detectors 22 will be described here. With reference to FIG. 5A, a hole 22*b* in which another end 353 of the optical fiber 21 is inserted, is formed in the detector 22. Here, the light entry end 352 of the optical fiber 21 is held in a corresponding one of the outlets 311 of the light applicator 20 (see FIG. 4). A holding part 22*a* for holding a cuvette 80, the hole 22*b*, and a communication hole 22*c* are formed in the detector 22. The communication hole 22*c* allows the hole 22*b* to be in communication with the holding part 22*a*.

The diameter of the hole 22*b* is larger than the diameter of the communication hole 22*c*. A lens 22*d* which condenses light from the optical fiber 21 is disposed at an end portion of the hole 22*b*. Further, an opening 22*f* is formed, in the inner wall surface of the holding part 22*a*, at a position opposed to the communication hole 22*c*. A light reception part 22*g* is disposed behind the opening 22*f*. The light reception part 22*g* is a photodiode and outputs an electric signal corresponding to the amount of received light. The light transmitted through the lens 22*d* enters a light reception surface of the light reception part 22*g* via the communication hole 22*c*, the holding part 22*a*, and the opening 22*f*. The optical fiber 21 is fixed by a plate spring 22*e* in a state where the other end 353 is inserted in the hole 22*b*.

With reference to FIG. 5B, when a cuvette 80 is held by the holding part 22*a*, the light condensed by the lens 22*d* is transmitted through the cuvette 80 and a sample accommodated in the cuvette 80 and enters the light reception part 22*g*. If a coagulation reaction progresses in the sample, the turbidity of the sample is increased. In association with this increase, the amount of light that is transmitted through the sample (transmitted light amount) is reduced, whereby the level of an electric signal that is outputted from the light reception part 22*g* is reduced. The electric signal outputted from the light reception part 22*g* is converted into a digital signal by an A/D converter 22*h*, and the digital signal is transmitted to the controller 24. The signal outputted from the light reception part 22*g* and converted by the A/D converter 22*h* is optical information reflecting the transmitted light amount.

Although the light reception part 22*g* of the detector 22 detects transmitted light in the above example, light scattered by the sample accommodated in the cuvette 80 (scattered light) may be received in the detector 22. In this case, the controller 10 analyzes the coagulation reaction on the basis of a change in the intensity of the scattered light. The detector 22 which detects scattered light has a configuration in which: an opening is provided in the inner surface of the holding part 22*a* so as to be located at the same height as that of the communication hole 22*c*; and a light detector is disposed behind the opening. When the cuvette 80 is held by the holding part 22*a* and light is applied to the cuvette 80, light having been scattered by the sample in the cuvette 80 is applied to the light detector via the opening. A detected signal from the light detector indicates the intensity of the scattered light having been scattered by the sample.

Figure 6:
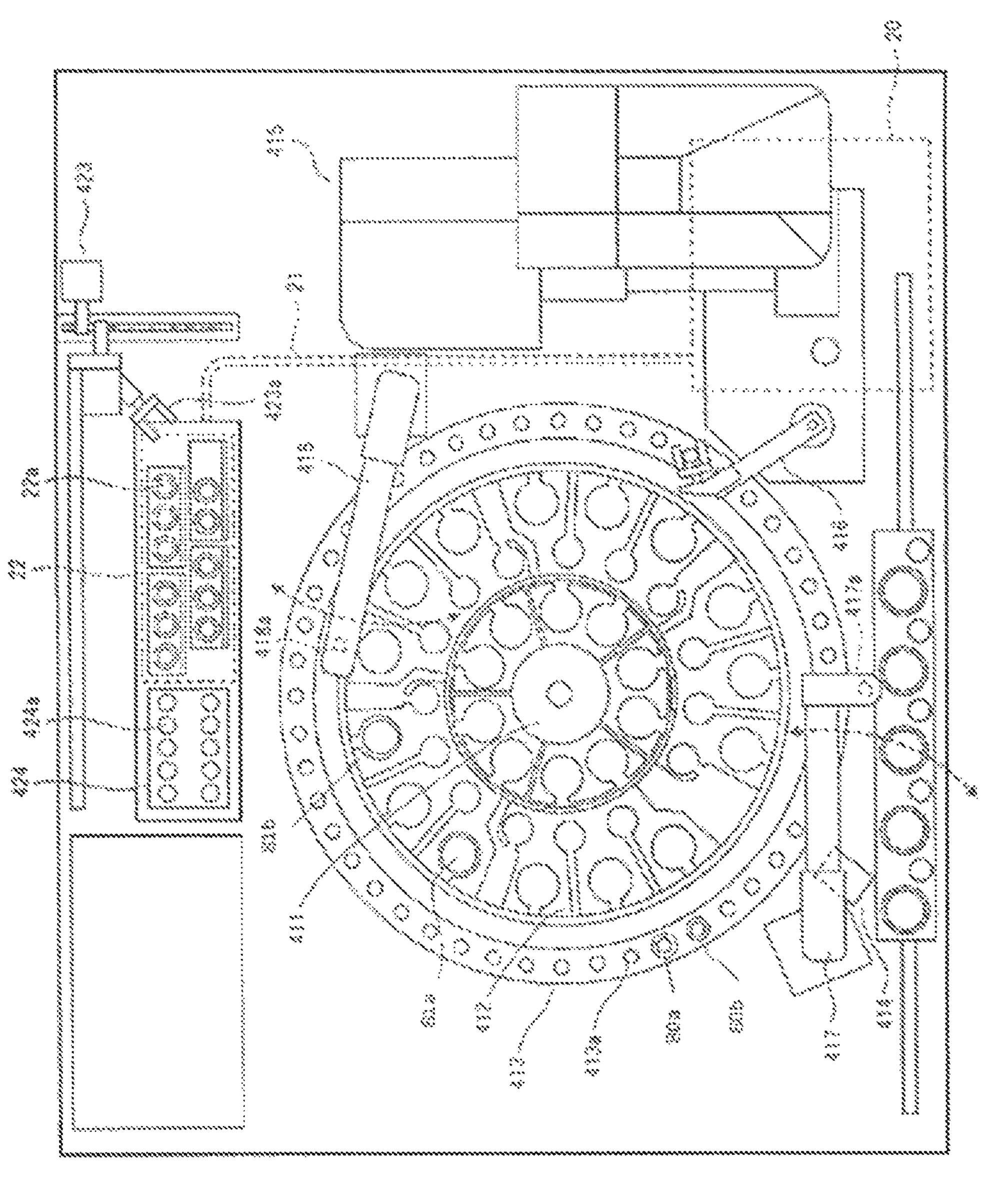
FIG. 6 is a plan view of a sample preparation part 23 as seen from above.

With reference to FIG. 6, the sample preparation part 23 will be described. Each of reagent tables 411 and 412 and a cuvette table 413 has an annular shape and is rotatably configured. The reagent tables 411 and 412 corresponds to reagent accommodating parts on which reagent containers 81*a* and 81*b* and the like are placed. A barcode label having a barcode printed thereon is pasted on each of the reagent containers 81*a* and 81*b* and the like. The barcode includes: the type of an accommodated reagent; and a reagent ID which is a serial number assigned to the reagent. The barcode on each of the reagent containers 81*a* and 81*b* placed on the reagent tables 411 and/or 412 is read by a barcode reader 414. The information (the type and the reagent ID of the reagent) read from the barcode is inputted to the controller 10 and stored in the storage 13 (see FIG. 2). The reagent container 81*a* in which an APTT measurement reagent is accommodated and the reagent container 81*b* in which a calcium solution is accommodated are placed on the reagent table 411 and/or 412.

Support portions 413*a* which are a plurality of openings capable of supporting cuvettes 80*a* and 80*b* and the like are formed in the cuvette table 413. The cuvettes 80*a* and 80*b* and the like having been newly set in a cuvette supply part 415 by a user are sequentially transferred by the cuvette supply part 415 and disposed in corresponding ones of the support portions 413*a* of the cuvette table 413 by a cuvette transfer part 416. The cuvettes 80*a* and 80*b* and the like have structures identical to one another.

A specimen dispensing arm 417 and a reagent dispensing arm 418 respectively have stepping motors connected thereto, so as to be movable upward and downward and so as to be rotatably movable. A pipette 417*a* having a tip that is sharply formed so as to be capable of puncturing a lid of a specimen container is disposed at the distal end of the specimen dispensing arm 417. A pipette 418*a* is disposed at the distal end of the reagent dispensing arm 418. A tip of the pipette 418*a* is flatly formed unlike the tip of the pipette 417*a*.

A heating part 424 includes a plurality of heat openings 424*a* and is configured to heat a sample accommodated in each of the cuvettes 80*a* and 80*b* and the like having been set in corresponding ones of the heat openings 424*a*. A cuvette transfer part 423 includes a catcher 423*a* for holding the cuvettes 80*a* and 80*b* and the like and is configured to transfer the cuvettes 80*a* and 80*b* and the like on the cuvette table 413 to corresponding ones of the heat openings 424*a* of the heating part 424 and corresponding ones of the holding parts 22*a* of the detector 22.

As the measurement device 200, a device described in U.S. Pat. No. 10,048,249 can be used. U.S. Pat. No. 10,048,249 is incorporated herein by reference.

1.3 Measurement Process and Analysis Process

A measurement process by the measurement device 200 is performed under the control of the controller 24, and an analysis process by the analyzer 100 is performed under the control of the controller 10. However, the present disclosure is not limited to this example. For example, the measurement process and the analysis process may be performed under the control of the controller 10, or the measurement process and the analysis process may be performed under the control of the controller 24.

Figure 7:
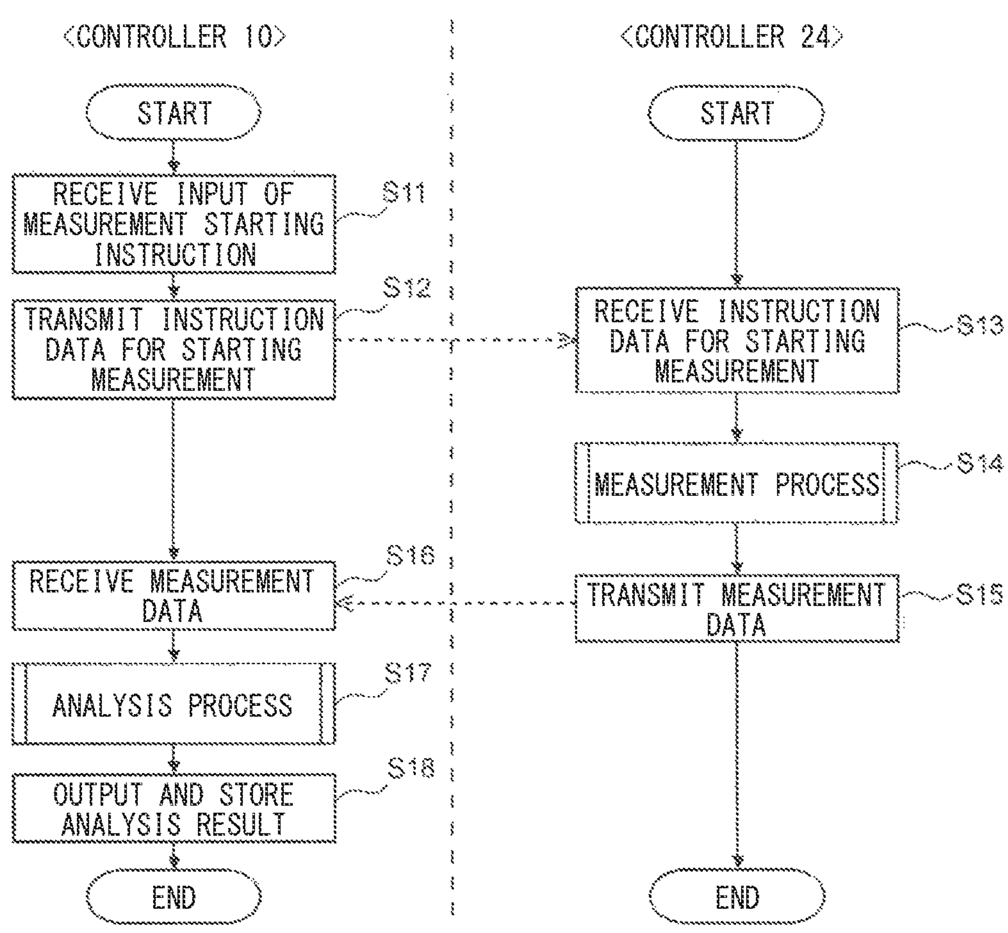
FIG. 7 is a flowchart showing processes to be performed by a controller 10 and a controller 24.

With reference to FIG. 7, in step S11, the controller 10 receives a measurement starting instruction which has been inputted through the input device 16 by a user. In step S12, the controller 10 transmits instruction data of the measurement starting instruction to the controller 24 of the measurement device 200. When the controller 24 receives the instruction data in step S13, the controller 24 executes a measurement process based on the measurement program in step S14. In step S15, the controller 24 transmits, to the controller 10, measurement data obtained through the measurement process, to end the process. In step S16, the controller 10 receives the measurement data and stores the measurement data in the storage 13. In step S17, the controller 10 executes an analysis process on the measurement data. In step S18, the controller 10 outputs an analysis result to the output device 17. In step S18, the controller 10 also stores the analysis result in the storage 13.

1.4 Measurement Process Based on Measurement Program (Step S14)

In step S14 of the measurement process, two samples are prepared from one blood specimen by using the same APTT measurement reagent, and a coagulation time of each of the samples is measured (that is, coagulation time measurement is performed two times). A waiting time from mixing of the blood specimen and the APTT measurement reagent to adding of a calcium solution differs between the two times of measurements. Specifically, the calcium solution is added to a first sample resulting from an elapse of a first waiting time from mixing of the blood specimen from the subject and the APTT measurement reagent, and a first coagulation time is measured. In addition, the calcium solution is added to a second sample resulting from an elapse of a second waiting time from mixing of the blood specimen and the APTT measurement reagent, and a second coagulation time is measured. Here, the second waiting time is a time longer than the first waiting time. The first and second waiting times will be described later. During the first and second waiting times, the first and second samples are respectively incubated. Incubation of the first and second samples is performed at a fixed temperature determined from, for example, a range of not lower than 30° C. and not higher than 42° C. Incubation of the first and second samples is preferably performed at 37° C.

The APTT measurement reagent refers to a reagent containing an activator and a phospholipid. The activator refers to a substance that activates a contact factor in the intrinsic coagulation pathway. Examples of the activator include an ellagic acid compound, silica, kaolin, Celite, and the like. The ellagic acid compound may be any of ellagic acid, an ellagic acid salt, and a metal complex of ellagic acid. These types of activators may be used singly, or two or more of these types of activators may be used in combination. The ellagic acid compound is preferably used as the activator. The ellagic acid compound is particularly preferably a metal complex of ellagic acid, containing metal ions such as zinc ions, manganese ions, or aluminum ions. Examples of the phospholipid include phosphatidylethanolamine (PE), phosphatidylcholine (PC), and phosphatidylserine (PS). The APTT measurement reagent contains one type of phospholipid selected from among PE, PC, and PS, preferably contains two types of phospholipids selected from among PE, PC, and PS, and more preferably contains all of these types of phospholipids. The phospholipid may be a naturally occurring phospholipid or a synthetic phospholipid.

As the APTT measurement reagent, commercially available reagents such as Revohem (registered trademark) APTT SLA (Sysmex Corporation), Thrombocheck (registered trademark) APTT SLA (Sysmex Corporation), Coagpia (registered trademark) APTT-N(Sekisui Medical Co., Ltd.), and Data-fi APTT (Siemens Healthcare Diagnostics Products GmbH), may be used.

The calcium solution is a reagent for starting blood coagulation by supplying calcium ions to a mixture of a blood specimen and the APTT measurement reagent. The calcium solution can be a calcium ion-containing aqueous solution. A preferable calcium solution is an aqueous solution of a calcium salt such as calcium chloride. The concentration of the calcium ions in the calcium solution is, for example, not lower than 10 mm and not higher than 30 mM, and preferably 20 mM or 25 mM. If a calcium salt easily soluble in water such as calcium chloride is used, the concentration of the calcium ions in the calcium solution can be expressed as the concentration of the calcium salt.

Figure 8:
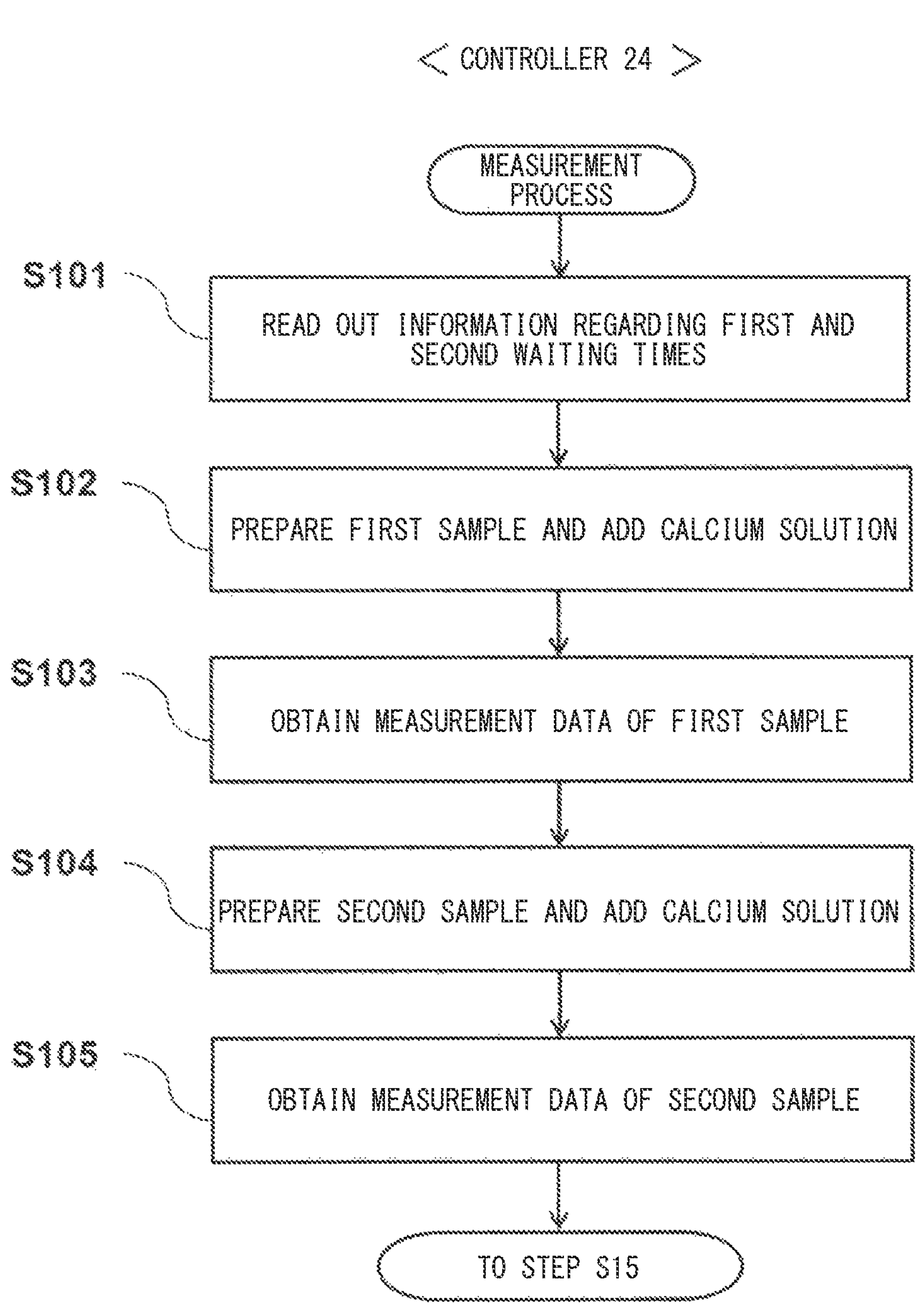
FIG. 8 is a flowchart showing a measurement process to be performed by the controller 24.

When step S11 shown in FIG. 7 is started, the controller 24 reads out the first and second waiting times in step S101 with reference to FIG. 8. In the present embodiment, the first and second waiting times are prestored in the solid-state drive of the controller 24, the first waiting time is 10 seconds, and the second waiting time is 30 seconds. Regarding the waiting times, input thereof may be received from a user through the input device 16, or the waiting times may be obtained via the network 98 from, for example, an electronic medical chart system 99 in a medical institution.

The first and second waiting times may be changed according to, for example, the type of the APTT measurement reagent. For example, each of the first and second waiting times may be determined from a range of not shorter than 10 seconds and shorter than 120 seconds. The first waiting time is, for example, not shorter than 10 seconds and not longer than 20 seconds. The second waiting time is, for example, longer than 20 seconds and not longer than 100 seconds and is longer than the first waiting time by at least 5 seconds. More specifically, the first waiting time can be 10, 11, 12, 13, 14, 15, 16, 17, 18, 19, or 20 seconds. Meanwhile, the second waiting time can be a time that is selected from among 20, 25, 30, 35, 40, 45, 50, 60, 70, 80, 90, or 100 seconds and that is longer than the first waiting time by at least 5, 10, 15, 20, 25, 30, 40, or 50 seconds.

Alternatively, each of the first and second waiting times may be determined from a range of longer than 140 seconds and not longer than 600 seconds. The first waiting time is, for example, longer than 150 seconds and not longer than 400 seconds. The second waiting time is, for example, longer than 400 seconds and not longer than 600 seconds and is longer than the first waiting time by at least 30 seconds. More specifically, the first waiting time can be 140, 150, 200, 250, 260, 270, 280, 290, 300, 305, 310, 315, 320, 330, 340, 350, or 400 seconds. Meanwhile, the second waiting time can be a time that is selected from among 400, 450, 500, 510, 520, 530, 540, 545, 550, 555, 560, 570, 580, 590, or 600 seconds and that is longer than the first waiting time by at least 50, 100, 150, 200, 210, 220, 230, 240, or 250 seconds.

With reference to FIG. 6 and FIG. 8, in step S102, the controller 24 controls the sample preparation part 23 to prepare a first sample and add the calcium solution to the prepared first sample. By this control, the pipette 417*a* of the specimen dispensing arm 417 suctions a blood specimen (plasma), from a subject, in a specimen container and dispenses the blood specimen into the cuvette 80*a*, which is empty, on the cuvette table 413. Then, the cuvette table 413 is rotated, the cuvette transfer part 423 transfers, to the heating part 424, the cuvette 80*a* containing the blood specimen from the subject, and the blood specimen in the cuvette 80*a* is heated to a predetermined temperature (37° C.). Then, the cuvette transfer part 423 transfers the cuvette 80*a* into a range within which the pipette 418*a* of the reagent dispensing arm 418 is movable, and the pipette 418*a* adds, into the cuvette 80*a*, the APTT measurement reagent suctioned from the reagent container 81*a*. Consequently, a first sample is prepared. The cuvette transfer part 423 returns the cuvette 80*a* to the heating part 424. Immediately before the first waiting time elapses from the adding of the APTT measurement reagent into the cuvette 80*a*, the cuvette transfer part 423 transfers, into the range within which the pipette 418*a* is movable, the cuvette 80*a* into which the APTT measurement reagent has been added. Then, after the first waiting time has elapsed from the adding of the APTT measurement reagent, the pipette 418*a* adds, into the cuvette 80*a*, the calcium solution suctioned from the reagent container 81*b*. Immediately after the adding of the calcium solution, the cuvette transfer part 423 transfers, into any of the holding parts 22*a* of the detector 22, the cuvette 80*a* into which the calcium solution has been added.

Figures 9, 10A:
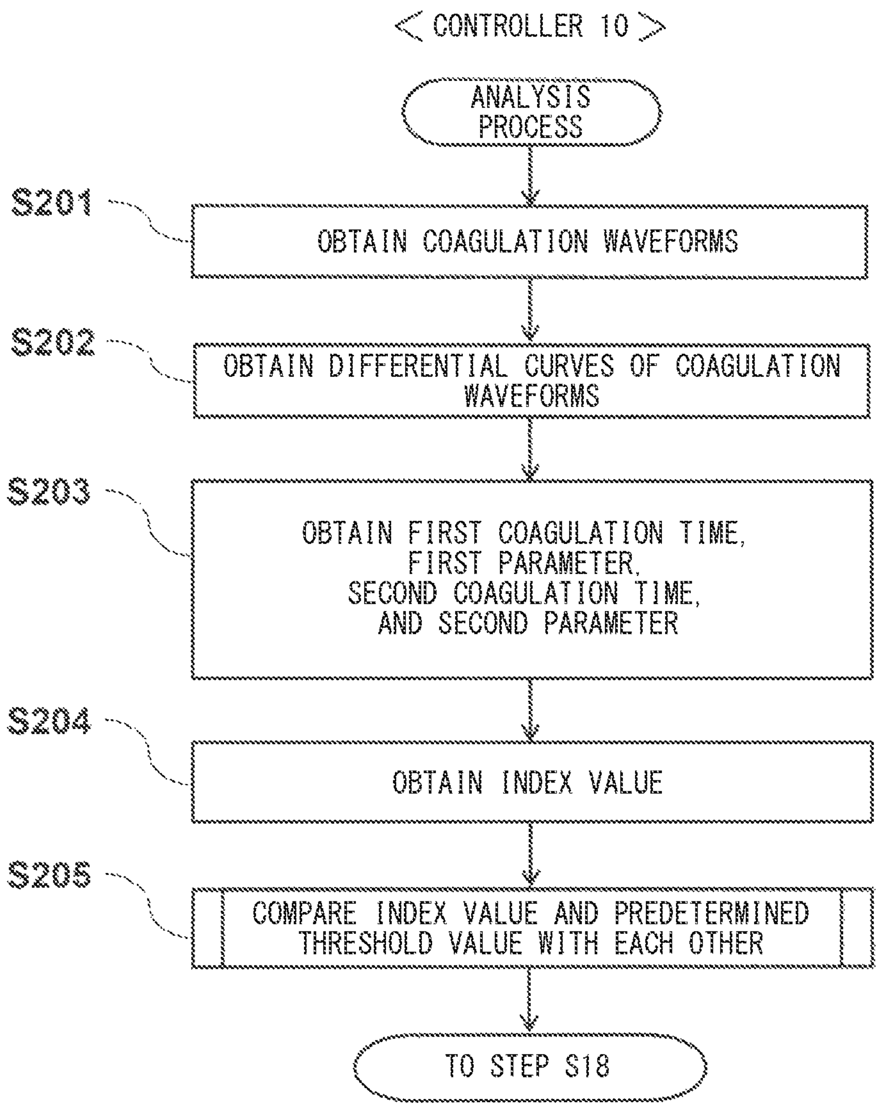
FIG. 9 is a flowchart showing an analysis process to be performed by the controller 10.
FIG. 10A shows an example of measurement data.

With reference to FIG. 4, FIG. 5B, FIG. 6, and FIG. 8, in step S103, the controller 24 controls the measurement device 200 to obtain measurement data of the first sample (first measurement data). By this control, the light applicator 20 applies light to the cuvette 80*a* transferred into the holding part 22*a*. In this example, only the first light source 321 applies light. The detector 22 transmits, to the controller 24, digital data corresponding to the intensity of received light. Specifically, the light reception part 22*g* outputs an analog signal corresponding to the intensity of the light received via the cuvette 80*a* and the sample in the cuvette 80*a* (transmitted light intensity), this signal is converted into a digital signal by the A/D converter 22*h*, and the digital signal is transmitted to the controller 24. The controller 24 continues to receive digital data from the time point of start of light application to the cuvette 80*a* until arrival at a predetermined measurement time (180 seconds). The time from the adding of the calcium solution to the cuvette 80*a* to the start of the light application is a time shorter than the first waiting time and the second waiting time (for example, shorter than 1 second), and thus the time point of the adding of the calcium solution to the cuvette 80*a* and the time point of the start of the light application can be regarded as substantially the same time point. The controller 24 associates a set of continuously received digital data with times having elapsed from the time point of the start of the light application to the cuvette 80*a*, and stores the associated data as measurement data of the first sample (first measurement data). A time interval at which the controller 24 receives the digital data is, for example, 0.1 seconds to 0.5 seconds. With reference to FIG. 10A, the measurement data is a set of two-dimensional array data including: an upper row indicating transmitted light intensities; and a lower row indicating times at which the respective transmitted light intensities are obtained (the times having elapsed from the time point of the start of the light application to the cuvette 80).

With reference to FIG. 6 and FIG. 8, in step S104, the controller 24 controls the sample preparation part 23 to prepare a second sample and add the calcium solution to the prepared second sample. By this control, the pipette 417*a* of the specimen dispensing arm 417 suctions the blood specimen (plasma), from the subject, in the specimen container and dispenses the blood specimen into the cuvette 80*b*, which is empty, on the cuvette table 413. Then, the cuvette table 413 is rotated, the cuvette transfer part 423 transfers, to the heating part 424, the cuvette 80*b* containing the blood specimen from the subject, and the blood specimen in the cuvette 80*b* is heated to the predetermined temperature (37° C.). Then, the cuvette transfer part 423 transfers the cuvette 80*b* into the range within which the pipette 418*a* of the reagent dispensing arm 418 is movable, and the pipette 418*a* adds, into the cuvette 80*b*, the APTT measurement reagent suctioned from the reagent container 81*a*. Consequently, a second sample is prepared. The cuvette transfer part 423 returns the cuvette 80*b* to the heating part 424. Immediately before the second waiting time elapses from the adding of the APTT measurement reagent into the cuvette 80*b*, the cuvette transfer part 423 transfers, into the range within which the pipette 418*a* is movable, the cuvette 80*b* into which the APTT measurement reagent has been added. Then, after the second waiting time has elapsed from the adding of the APTT measurement reagent, the pipette 418*a* adds, into the cuvette 80*b*, the calcium solution suctioned from the reagent container 81*b*. Immediately after the adding of the calcium solution, the cuvette transfer part 423 transfers, into any of the holding parts 22*a* of the detector 22, the cuvette 80*b* into which the calcium solution has been added. The time from adding of the calcium solution to the cuvette to completion of transfer of the cuvette to the holding part 22*a* of the detector 22 is the same between the first sample and the second sample.

With reference to FIG. 4, FIG. 5B, FIG. 6, and FIG. 8, in step S105, the controller 24 controls the measurement device 200 to obtain measurement data of the second sample (second measurement data). By this control, the light applicator 20 applies light to the cuvette 80*b* transferred into the holding part 22*a*. In this example, only the first light source 321 applies light. The detector 22 transmits, to the controller 24, digital data corresponding to the intensity of received light. The controller 24 continues to receive digital data from the time point of the adding of the calcium solution into the cuvette 80*b* until arrival at the predetermined measurement time (180 seconds). The controller 24 associates a set of continuously received digital data with times having elapsed from the time point of the start of the light application to the cuvette 80*b*, and stores the associated data as measurement data of the second sample (second measurement data). The data structure of the second measurement data is the same as that of the first measurement data. When processing in step S105 is ended, the controller 24 advances the process to step S15. As described above, in step S15, the controller 24 transmits the measurement data obtained through the measurement process to the controller 10, and, in step S16, the controller 10 receives the measurement data and stores the measurement data in the storage 13.

1.5 Analysis Process Based on Analysis Program (Step S17)

Figure 10B:
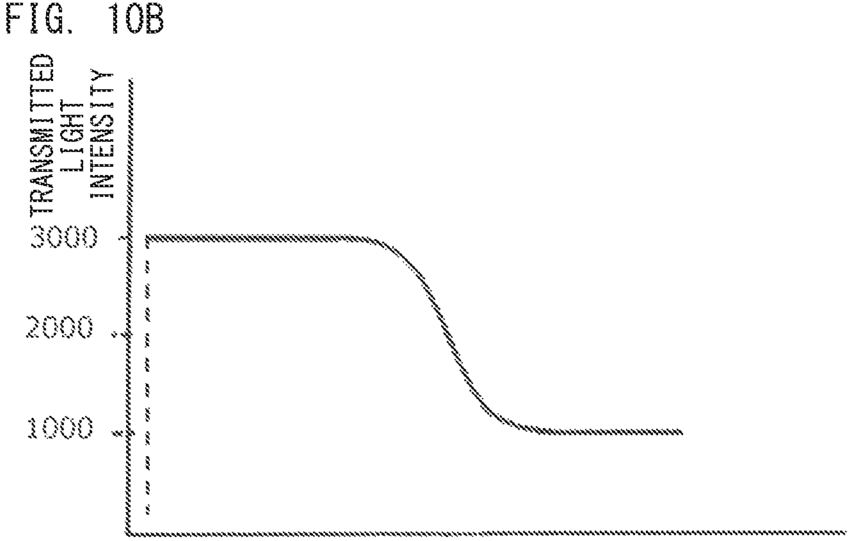
FIG. 10B shows an example of a coagulation waveform.
Figure 10C:
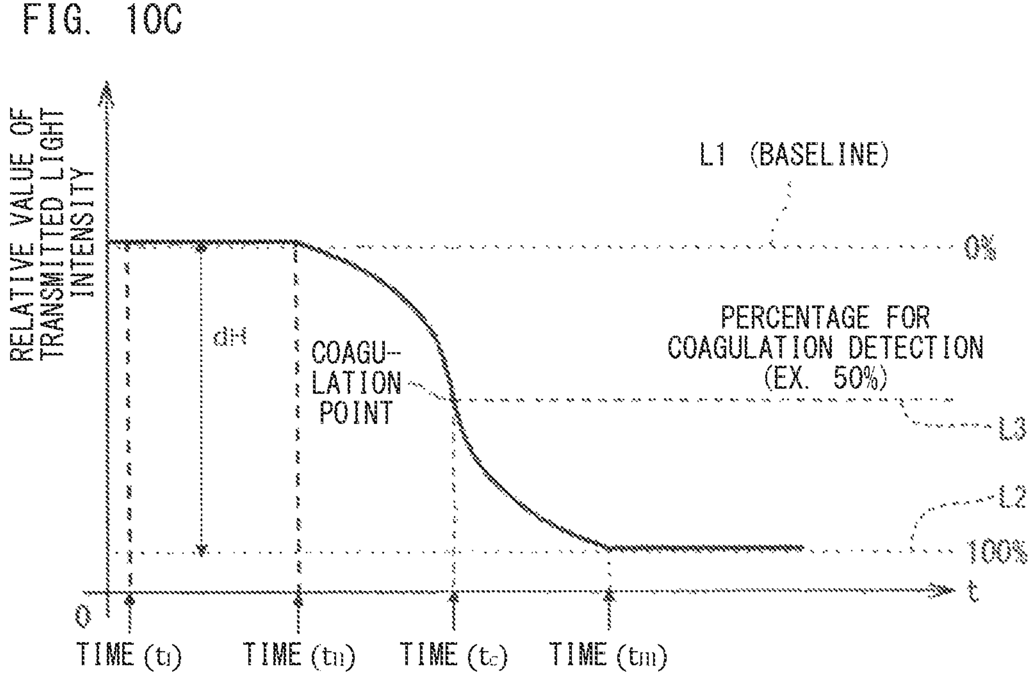
FIG. 10C shows an example of a normalized coagulation waveform.

When step S17 shown in FIG. 7 is started, the controller 10 reads out the measurement data (the first measurement data and the second measurement data) stored in the storage 13, in step S201 with reference to FIG. 9. The controller 10 plots the read-out first measurement data onto a two-dimensional graph having: a vertical axis (Y axis) indicating the transmitted light intensity; and a horizontal axis (X axis) indicating the measurement time (seconds: sec) over which the transmitted light intensity is monitored. Consequently, the controller 10 obtains a first coagulation waveform as shown in FIG. 10B. Further, the controller 10 normalizes the obtained first coagulation waveform. With reference to FIG. 10C, in the normalized first coagulation waveform, each transmitted light intensity included in the first measurement data is expressed as a relative value so as to be shown between 0% (L1: baseline) and 100% (L2) of the vertical axis. Regarding the second measurement data as well, the controller 10 obtains a second coagulation waveform and normalizes the obtained second coagulation waveform in the same manner.

Figure 11A:
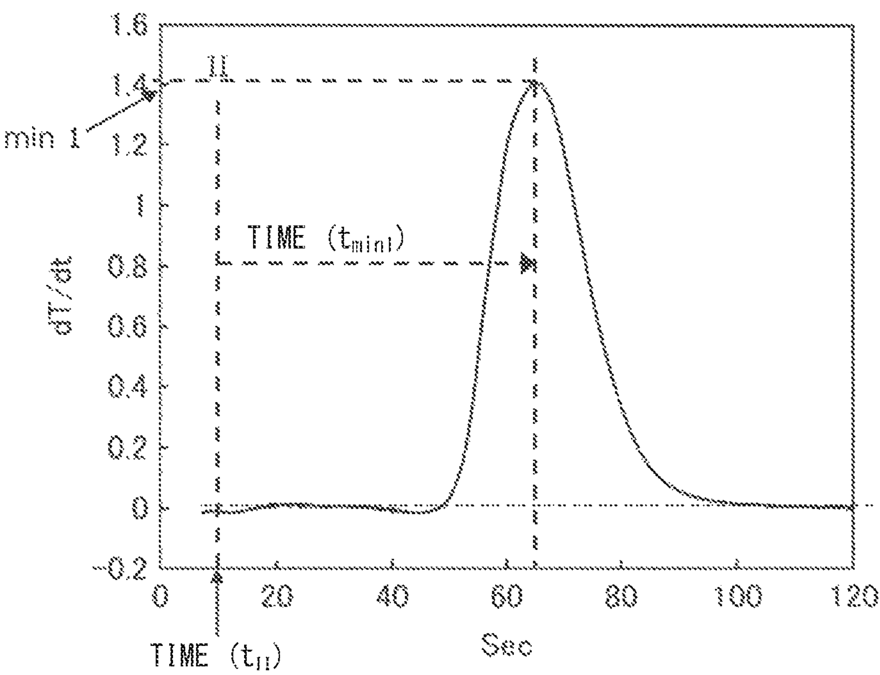
FIG. 11A shows an example of a first-order differential curve of the coagulation waveform.
Figure 11B:
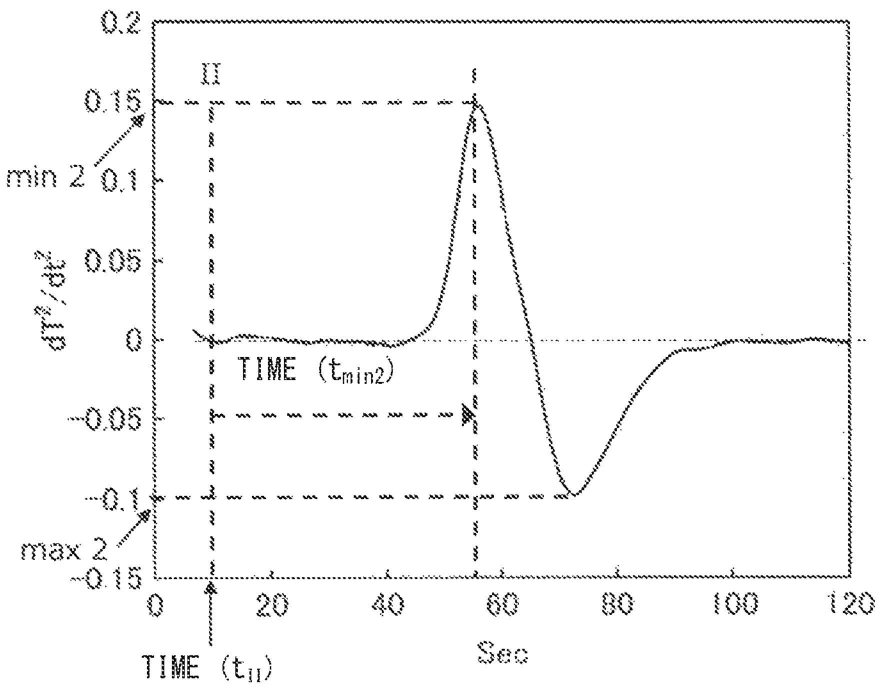
FIG. 11B shows an example of a second-order differential curve of the coagulation waveform.

In step S202, the controller 10 differentiates the normalized first coagulation waveform to obtain a first-order differential curve of the coagulation waveform as shown in FIG. 11A. The controller 10 further differentiates the first-order differential curve to obtain a second-order differential curve of the coagulation waveform as shown in FIG. 11B. Regarding the second measurement data as well, the controller 10 obtains a first-order differential curve of the corresponding coagulation waveform and a second-order differential curve of the corresponding coagulation waveform in the same manner. In step S201, normalization of the coagulation waveforms can be omitted. In this case, the controller 10 obtains a first-order differential curve by differentiating the coagulation waveform not having been normalized (see FIG. 10B). Although the first-order differential curve is expressed such that a coagulation speed (dT/dt) takes positive values in FIG. 11A, the first-order differential curve may be expressed such that the coagulation speed takes negative values. The same applies to the second-order differential curve. That is, curves with positive and negative values thereof in the vertical axis being inverted from those of the curves in FIG. 11A and FIG. 11B, may be obtained.

In step S203, the controller 10 obtains a first coagulation time and a first parameter regarding either of the differentials of the first coagulation waveform (hereinafter, referred to as "first parameter"), for the first sample, and obtains a second coagulation time and a second parameter regarding either of the differentials of the second coagulation waveform (hereinafter, referred to as "second parameter"), for the second sample. Each of the first coagulation time and the second coagulation time is, for example, a time from the adding of the calcium solution to the corresponding sample obtained by mixing of the blood specimen and the APTT measurement reagent to attainment of a predetermined coagulation state. Each of the first and second parameters is a parameter obtained from the first-order differential curve or the second-order differential curve of the corresponding coagulation waveform. The parameter obtained from the first-order differential curve is a value regarding a coagulation speed, and the parameter obtained from the second-order differential curve is a value regarding a coagulation acceleration or a coagulation deceleration.

With reference to FIG. 10C, obtainment of a first coagulation time $t_c$ will be described. In the first coagulation waveform obtained in step S201, a time $t_1$ is a time point at which the calcium solution has been added to the sample, and fibrin deposition has not occurred at the time $t_1$. Therefore, the transmitted light intensity takes a high value at the time $t_1$. Thereafter, when a coagulation reaction progresses and fibrin deposition starts, deposited fibrin blocks the light so that the transmitted light intensity starts to be reduced. This time point is a time $t_{11}$ which is a coagulation reaction start time. The controller 10 obtains, through an arithmetic operation, a time at which the transmitted light intensity starts to be reduced in the coagulation waveform. The controller 10 sets this time as the time $t_{11}$. The controller 10 sets, as 0%, the amount of change in the transmitted light intensity at the time $t_{11}$.

Thereafter, as fibrin deposition progresses, the transmitted light intensity is further reduced. When most of fibrinogen in the sample turn into fibrin, the reaction converges so that the coagulation waveform plateaus. The controller 10 obtains, through an arithmetic operation, a time at which the coagulation waveform starts to plateau. The controller 10 sets this time as a time $t_{III}$. The time $t_{III}$ is a coagulation reaction end time. The controller 10 sets, as 100%, the amount of change in the transmitted light intensity at the time $t_{III}$. Then, the controller 10 sets, as a time $t_c$, a time at which the amount of change in the transmitted light intensity is 50% (a time at an intersection point between a line L3 and the coagulation waveform). The controller 10 obtains this time as the first coagulation time. The coagulation time is not limited to a time at which the amount of change in the transmitted light intensity is 50%, and a time at which the amount of change is an arbitrarily-selected value such as 30%, 40%, 60%, or 70% may be obtained as the coagulation time. Alternatively, the coagulation time (time $t_c$) may be, for example, a time after a constant time counted from the time $t_{II}$ which is the coagulation reaction start time. If normalization of the coagulation waveform is omitted, the controller 10 obtains the first coagulation time $t_c$ from the coagulation waveform not having been normalized. The controller 10 also obtains the second coagulation time on the basis of the second coagulation waveform through the same method as that for the first coagulation time $t_c$.

In step S203, the controller 10 obtains, through an arithmetic operation, the first parameter on the basis of the first-order differential curve and/or the second-order differential curve, of the first coagulation waveform, which have been obtained in step S202. Examples of the first parameter include, but are not limited to, |min 1|, |min 2|, |max 2|, a maximum speed arrival time ($t_{min1}$), a maximum acceleration arrival time ($t_{min2}$), and the like. As shown in FIG. 11A, |min 1| is the absolute value of a peak value (min1) of the coagulation speed in the first-order differential curve and indicates a maximum coagulation speed. $t_{min1}$ is a time from the coagulation reaction start time (time $t_{II}$) to arrival at the maximum coagulation speed, in the first-order differential curve. As shown in FIG. 11B, |min 2| is the absolute value of a peak value of the coagulation acceleration in the second-order differential curve and indicates a maximum coagulation acceleration. |max 2| is the absolute value of a peak value (min2) of the coagulation deceleration in the second-order differential curve and indicates a maximum coagulation deceleration. $t_{min2}$ is a time from the coagulation reaction start time (time $t_{II}$) to arrival at the maximum coagulation acceleration, in the second-order differential curve. The controller 10 also obtains the second parameter on the basis of the first-order differential curve and/or the second-order differential curve of the second coagulation waveform through the same method as that for the first parameter. In the present embodiment, obtainment of the first-order differential curve and the second-order differential curve in step S202, and obtainment of the first and second parameters in step S203, may be omitted.

In S204, the controller 10 obtains at least one index value based on the coagulation times and/or the parameters obtained in step S203. This index value is a value that is changed according to the cause of coagulation time prolongation. For example, the index value can indicate that the blood specimen from the subject is suspected of containing LA or heparin. Alternatively, the index value can indicate that the blood specimen from the subject is suspected of containing heparin. Alternatively, the index value can indicate that the blood specimen from the subject is suspected of having a cause of prolongation other than LA and heparin.

The controller 10 obtains, through an arithmetic operation, an index value by using the coagulation times and/or the values of the parameters obtained in step S203. Mathematical expressions for calculating the index value are stored in the function database DB1 (FIG. 3). An index value 1 as an example of the index value is, for example, a value calculated by using the following mathematical expression 1. In the mathematical expression, "−" indicates subtraction.

(Index value 1)=(first coagulation time)−(second coagulation time) (mathematical expression 1)

In step S205, the controller 10 compares the index value obtained in step S204 and a predetermined threshold value with each other, and determines a cause of prolonging the coagulation reaction. The predetermined threshold value is a reference value according to which a cause of coagulation time prolongation of the blood specimen is determined. The predetermined threshold value is stored in the threshold value database DB2 (FIG. 3) of the storage 13. A determination result for the cause of prolonging the coagulation reaction is outputted by the output device 17 in step S18 (FIG. 7).

The predetermined threshold value is preset correspondingly to the mathematical expression. For example, if a first index value is a value obtained by subtracting the second coagulation time from the first coagulation time (the value calculated by using the mathematical expression 1), this value and a first threshold value are compared with each other.

Figure 12A:
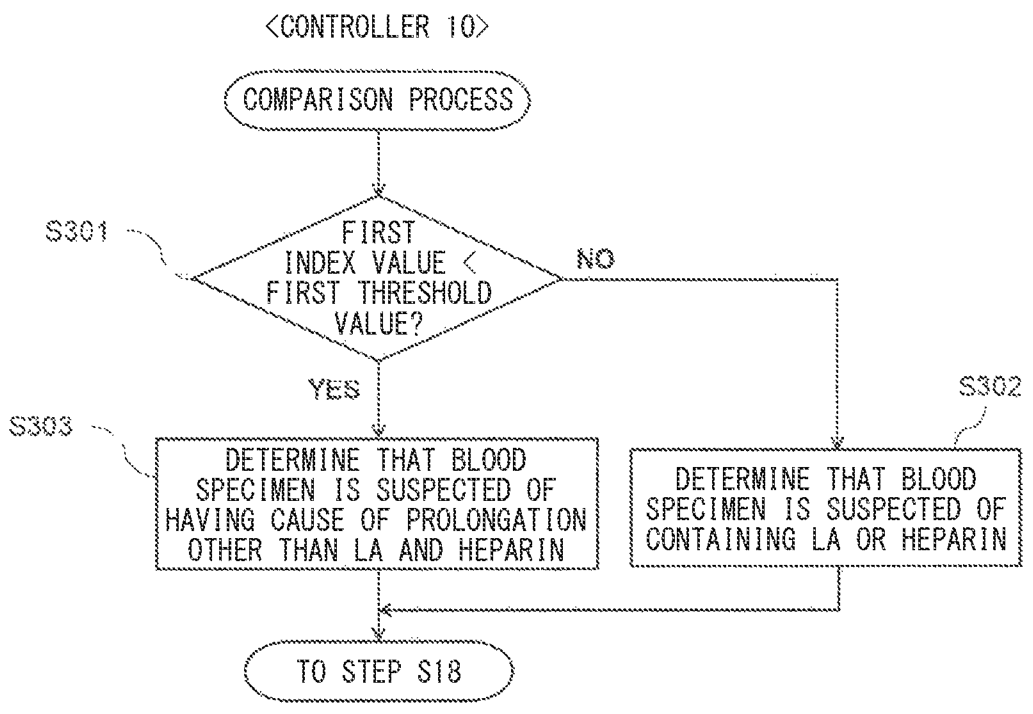
FIG. 12A is a flowchart showing a comparison process to be performed by the controller 10.

With reference to FIG. 12A, a comparison process in step S205 will be described. In step S301, the first index value and the first threshold value are compared with each other, and, in a case where the first index value is not lower than the first threshold value (in the case of "NO"), the controller 10 advances the process to step S302 in which the controller 10 determines that the blood specimen is suspected of containing LA or heparin. In step S301, in a case where the first index value is lower than the first threshold value (in the case of "YES"), the controller 10 advances the process to step S303 in which the controller 10 determines that the blood specimen is suspected of having a cause of prolongation other than LA and heparin. For example, in a case where the first coagulation time is a coagulation time of a sample for which the waiting time is 10 seconds, and the second coagulation time is a coagulation time of a sample for which the waiting time is 30 seconds, the first threshold value may be 10 seconds. The first index value may be calculated by using the following mathematical expression 2 instead of the mathematical expression 1.

(Index value 1')=(second coagulation time)−(first coagulation time) (mathematical expression 2)

1.6 Modifications of Comparison Process (Step S205)

Hereinafter, modifications of the comparison process in step S205 will be described. An index value 2 as an example of the index value can be, for example, a value calculated by using the following mathematical expression 3. In the mathematical expression, "−" indicates subtraction. In the present embodiment, each of the first parameter and the second parameter is |min 1|.

(Index value 2)=(value of first parameter)−(value of second parameter) (mathematical expression 3)

A predetermined threshold value is preset according to the mathematical expression. For example, if a second index value is a value obtained by subtracting the value of the second parameter from the value of the first parameter (the value calculated by using the mathematical expression 3), this value and a second threshold value are compared with each other.

Figure 12B:
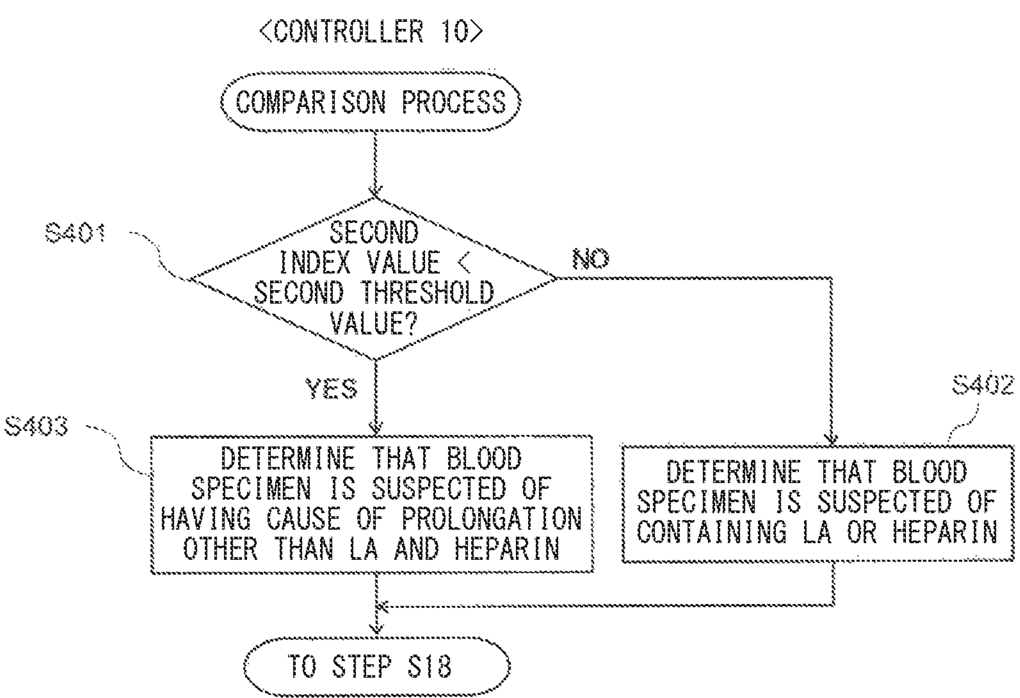
FIG. 12B is a flowchart showing a comparison process to be performed by the controller 10.

With reference to FIG. 12B, in step S401, the second index value and the second threshold value are compared with each other, and, in a case where the second index value is not lower than the second threshold value (in the case of "NO"), the controller 10 advances the process to step S402 in which the controller 10 determines that the blood specimen is suspected of containing LA or heparin. In step S401, in a case where the second index value is lower than the second threshold value (in the case of "YES"), the controller 10 advances the process to step S403 in which the controller 10 determines that the blood specimen is suspected of having a cause of prolongation other than LA and heparin. The second index value may be calculated by using the following mathematical expression 4 instead of the mathematical expression 3.

(Index value 2')=(value of second parameter)−(value of first parameter) (mathematical expression 4)

The index value is not limited to the values calculated by using mathematical expressions exemplified by the mathematical expressions 1 to 4. The index value can be, for example, any of values calculated by using the following mathematical expressions. In the mathematical expressions, "/" indicates division.

(Index value 3)=(first coagulation time)/(second coagulation time) (mathematical expression 5)

(Index value 3')=(second coagulation time)/(first coagulation time) (mathematical expression 6)

(Index value 4)=(value of first parameter)/(value of second parameter) (mathematical expression 7)

(Index value 4')=(value of second parameter)/(value of first parameter) (mathematical expression 8)

Further modifications of the index values calculated by using the above mathematical expressions may be, for example, a value obtained by multiplying, by a constant, a value calculated by using any of the above mathematical expressions 1 to 8, a value obtained by adding a constant to a value calculated by using any of the above mathematical expressions, a value obtained by subtracting a constant from a value calculated by using any of the above mathematical expressions, a reciprocal of a value calculated by using any of the above mathematical expressions, a value obtained by combining these calculations, and the like. The constant is not particularly limited and can be, for example, an arbitrarily-selected natural number. Alternatively, the value of a coagulation time, of the blood specimen from the subject, obtained in ordinary APTT measurement (with a waiting time of, for example, 130 seconds) may be used as the constant.

Predetermined threshold values corresponding to the respective index values are not particularly limited. For example, the predetermined threshold values can be empirically set by obtaining first and second coagulation times and first and second parameters and accumulating data of index values for specimens having known causes of coagulation time prolongation, such as LA-positive specimens, heparin-containing specimens, coagulation factor-deficient specimens, warfarin-containing specimens, and DOAC-containing specimens. Alternatively, index values may be obtained for each of an LA-positive specimen group, a heparin-containing specimen group, and specimen groups having causes of prolongation other than LA and heparin, and a value that enables clear distinction between these groups may be set as a predetermined threshold value. A method for setting the threshold values is not particularly limited, and the threshold values may be set through, for example, ROC analysis. In threshold value setting performed through ROC analysis, ROC curves among which threshold value candidates differ may be drawn on a graph having a vertical axis indicating sensitivity and a horizontal axis indicating 1-specificity, and a threshold value candidate corresponding to a point on the ROC curve closest to a point at which the sensitivity is 1 and the 1-specificity is 0, may be set as a predetermined threshold value.

The first and second waiting times do not need to be 10 seconds and 30 seconds, and can be various times as described above. Hereinafter, a case where each of the first and second waiting times is longer than 140 seconds and not longer than 600 seconds (for example, the first waiting time is 310 seconds, and the second waiting time is 550 seconds) will be described as an example.

Figure 12C:
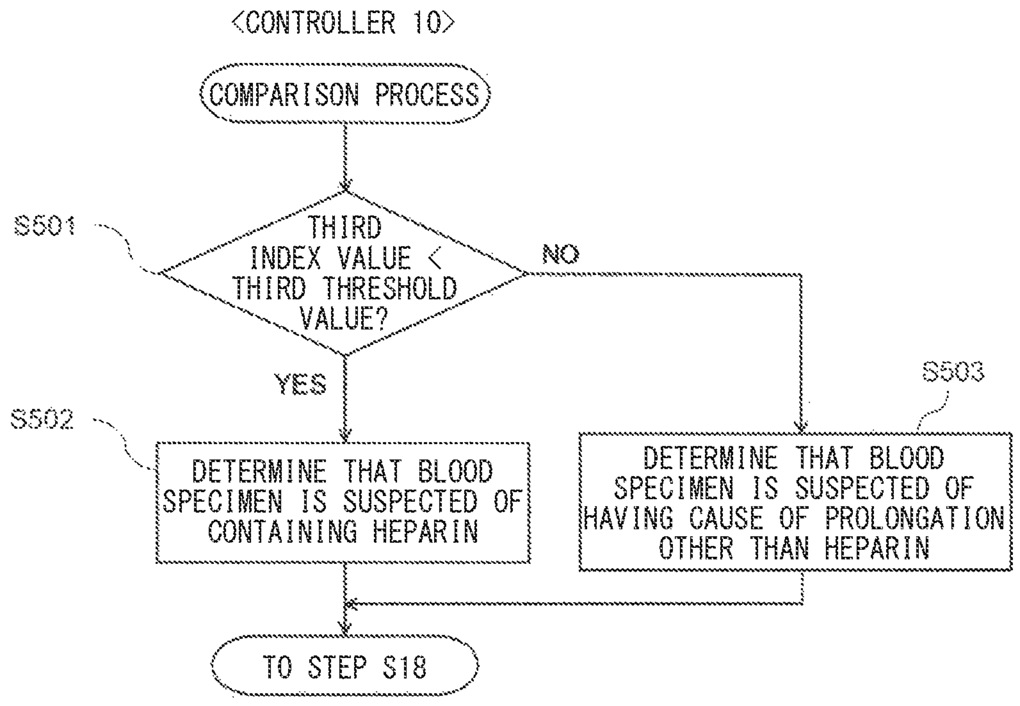
FIG. 12C is a flowchart showing a comparison process to be performed by the controller 10.

FIG. 12C shows a comparison process in a case where: each of the first and second waiting times is longer than 140 seconds and not longer than 600 seconds (for example, the first waiting time is 310 seconds, and the second waiting time is 550 seconds); and a third index value is the value of the ratio of the first coagulation time to the second coagulation time (the value calculated by using the mathematical expression 5). In step S501, the third index value and a third threshold value are compared with each other, and, in a case where the third index value is lower than the third threshold value (in the case of "YES"), the controller 10 advances the process to step S502 in which the controller 10 determines that the blood specimen is suspected of containing heparin. In step S501, in a case where the third index value is not lower than the third threshold value (in the case of "NO"), the controller 10 advances the process to step S503 in which the controller 10 determines that the blood specimen is suspected of having a cause of prolongation other than heparin.

Figure 12D:
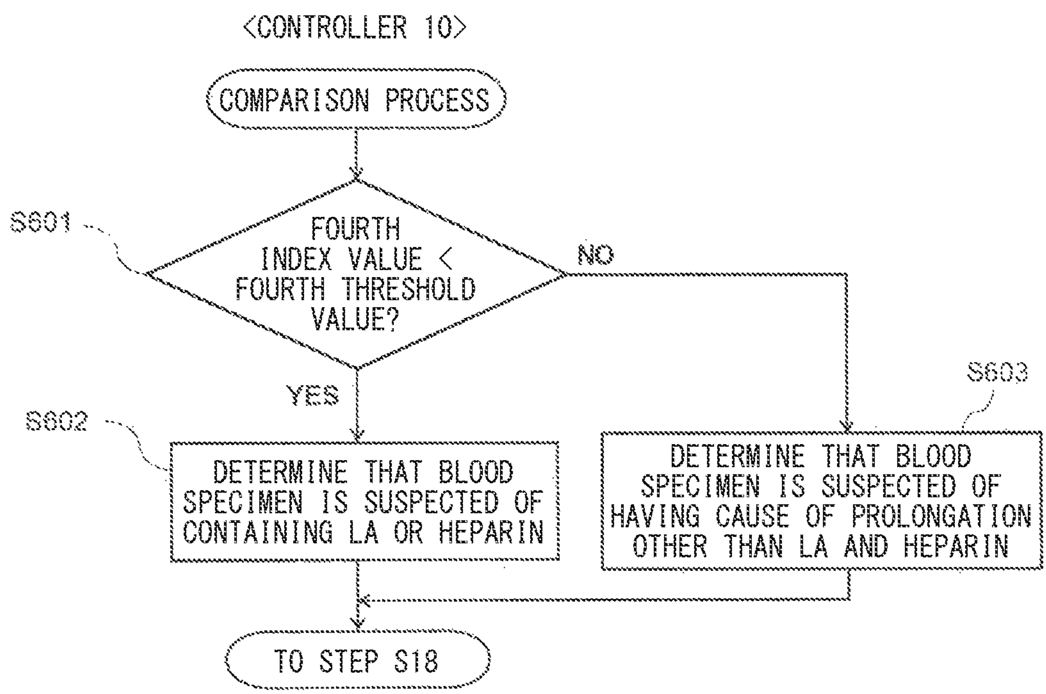
FIG. 12D is a flowchart showing a comparison process to be performed by the controller 10.

FIG. 12D shows a comparison process in a case where: each of the first and second waiting times is longer than 140 seconds and not longer than 600 seconds (for example, the first waiting time is 310 seconds, and the second waiting time is 550 seconds); and a fourth index value is the value of the ratio of the value of the first parameter to the value of the second parameter (the value calculated by using the mathematical expression 7). In step S601, the fourth index value and a fourth threshold value are compared with each other, and, in a case where the fourth index value is lower than the fourth threshold value (in the case of "YES"), the controller 10 advances the process to step S602 in which the controller 10 determines that the blood specimen is suspected of containing LA or heparin. In step S601, in a case where the fourth index value is not lower than the fourth threshold value (in the case of "NO"), the controller 10 advances the process to step S603 in which the controller 10 determines that the blood specimen is suspected of having a cause of prolongation other than LA and heparin.

A comparison process in a case of having obtained two index values will be described. FIG. 12E shows a comparison process in a case where: each of the first and second waiting times is longer than 140 seconds and not longer than 600 seconds (for example, the first waiting time is 310 seconds, and the second waiting time is 550 seconds); the third index value is the value of the ratio of the first coagulation time to the second coagulation time (the value calculated by using the mathematical expression 5); and the fourth index value is the value of the ratio of the value of the first parameter to the value of the second parameter (the value calculated by using the mathematical expression 7). In step S701, the third index value and the third threshold value are compared with each other, and, in the case where the third index value is lower than the third threshold value (in the case of "NO"), the controller 10 advances the process to step S702 in which the controller 10 determines that the blood specimen is suspected of containing heparin. In step S701, in the case where the third index value is not lower than the third threshold value (in the case of "YES"), the controller 10 advances the process to step S703.

In step S703, the fourth index value and the fourth threshold value are compared with each other, and, in the case where the fourth index value is lower than the fourth threshold value (in the case of "NO"), the controller 10 advances the process to step S704 in which the controller 10 determines that the blood specimen is suspected of containing LA. In step S703, in the case where the fourth index value is not lower than the fourth threshold value (in the case of "YES"), the controller 10 advances the process to step S705 in which the controller 10 determines that the blood specimen is suspected of having a cause of prolongation other than LA and heparin.

When the processing in step S205 is completed, the controller 10 returns the process to step S18 (FIG. 7), outputs a result of the comparison process to the output device 17 as information regarding a cause of coagulation time prolongation, and stores the result in the storage 13. In the case where the comparison result in step S301 is "YES", in the case where the comparison result in step S401 is "YES", in the case where the comparison result in step S601 is "NO", and in the case where the comparison result in step S703 is "YES", the result of the comparison process outputted to the output device 17 may be, for example, "suspicion of having a cause of prolongation other than mixing of LA and mixing of heparin". In the case where the comparison result in step S501 is "NO", the result of the comparison process outputted to the output device 17 may be, for example, "suspicion of having a cause of prolongation other than mixing of heparin". In the case where the comparison result in step S301 is "NO", in the case where the comparison result in step S401 is "NO", and in the case where the comparison result in step S601 is "YES", the result of the comparison process outputted to the output device 17 may be, for example, "suspicion of mixing of LA or heparin". In the case where the comparison result in step S501 is "YES" and in the case where the comparison result in step S701 is "NO", the result of the comparison process outputted to the output device 17 may be, for example, "suspicion of mixing of heparin". In the case where the comparison result in step S703 is "NO", the result of the comparison process outputted to the output device 17 may be, for example, "suspicion of LA". The result of the comparison process outputted to the output device 17 may be, for example, displayed as characters such as "suspicion of LA" or "suspicion of mixing of heparin", or as a pictorial mark or a symbol such as a flag.

With reference to FIG. 7 and FIG. 9, in step S18, the controller 10 may output, as information regarding a cause of coagulation time prolongation, the index value obtained in step S204 to the output device 17 without performing step S205. Alternatively, in step S18, the controller 10 may output, as information regarding a cause of coagulation time prolongation, the index value obtained in step S204 to the output device 17 also in the case of performing step S205. Alternatively, in step S18, the controller 10 may output, as information regarding a cause of coagulation time prolongation, the index value obtained in step S204 and the result of the comparison process obtained in step S205.

1.7 Modifications of Measurement Process and Analysis Process

In the measurement process, four samples are prepared from the one blood specimen by using the same APTT measurement reagent, and a coagulation time of each of the samples is measured (that is, coagulation time measurement is performed four times). Specifically, measurement of a third coagulation time and a fourth coagulation time is performed in addition to measurement of the first and second coagulation times. In this case, the calcium solution is added to a third sample resulting from an elapse of a third waiting time from mixing of the blood specimen from the subject and the APTT measurement reagent, and the third coagulation time is measured. In addition, the calcium solution is added to a fourth sample resulting from an elapse of a fourth waiting time from mixing of the blood specimen and the APTT measurement reagent, and the fourth coagulation time is measured. Here, the third waiting time is a time longer than the second waiting time, and the fourth waiting time is a time longer than the third waiting time. The incubation temperature for the third and fourth samples is the same as the incubation temperature for the first and second samples.

In the above modification, at least one of the first and second waiting times is shorter than a waiting time in ordinary APTT measurement, and the third and fourth waiting times are longer than the waiting time in ordinary APTT measurement. Specifically, each of the first and second waiting times is determined from a range of not shorter than 10 seconds and shorter than 120 seconds, and each of the third and fourth waiting times is determined from a range of longer than 140 seconds and not longer than 600 seconds. The first waiting time is, for example, not shorter than 10 seconds and not longer than 20 seconds. The second waiting time is, for example, longer than 20 seconds and not longer than 100 seconds and is longer than the first waiting time by at least 5 seconds. The third waiting time is, for example, longer than 150 seconds and not longer than 400 seconds. The fourth waiting time is, for example, longer than 400 seconds and not longer than 600 seconds and is longer than the third waiting time by at least 30 seconds. The same descriptions as those made above regarding the first and second waiting times apply to more detailed exemplification of each of the waiting times.

Figure 13A:
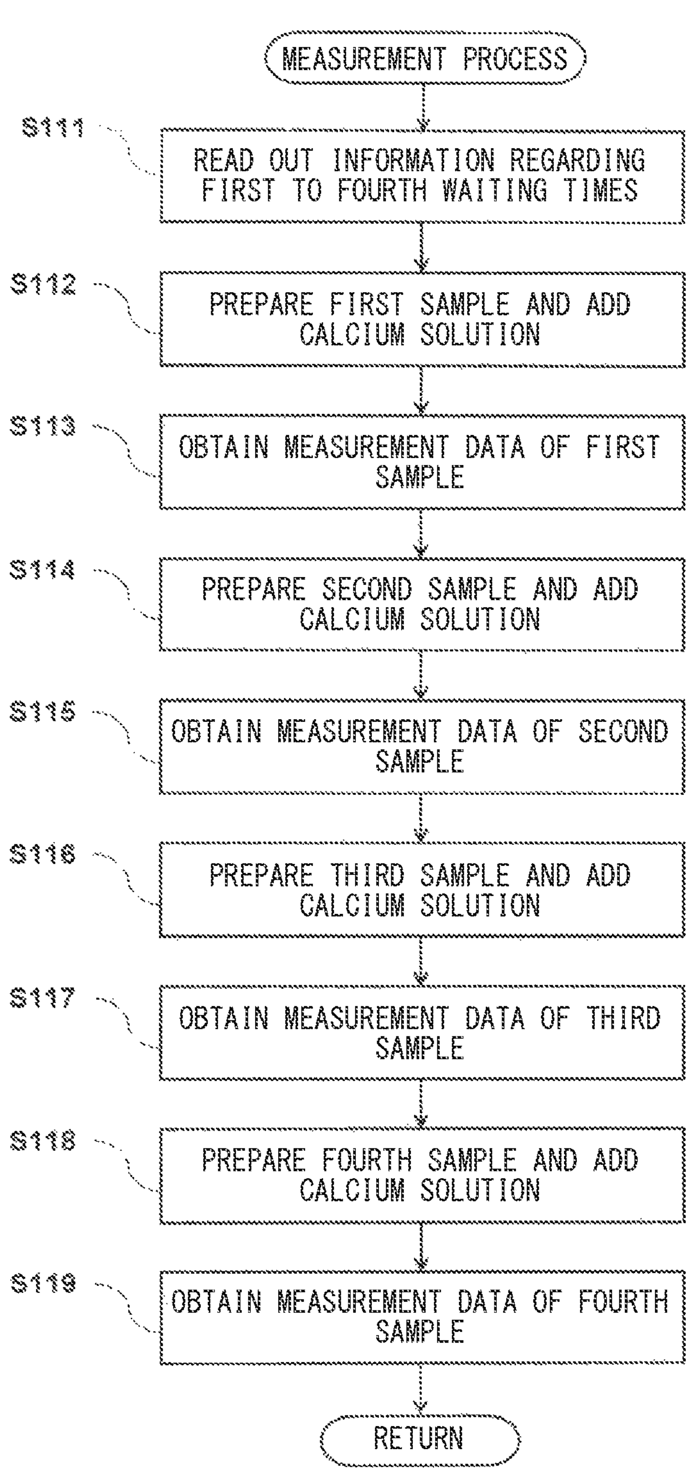
FIG. 13A is a flowchart showing a measurement process to be performed by the controller 24.

With reference to FIG. 13A, a measurement process in the above modification will be described. In step S111, the controller 24 reads out the first to fourth waiting times. From step S112 to step S115, the controller 24 executes the same process as that from step S102 to step S105. In step S116, the controller 24 performs the same processing as that in step S102 such that a third sample is prepared by adding the APTT measurement reagent to the blood specimen. In addition, in step S116, the controller 24 controls the sample preparation part 23 to add the calcium solution to the third sample after the third waiting time has elapsed from the adding of the APTT measurement reagent. In step S117, the controller 24 performs the same processing as that in step S103 such that measurement data of the third sample (third measurement data) is obtained from the third sample to which the calcium solution has been added in step S116. In step S118, the controller 24 performs the same processing as that in step S102 such that a fourth sample is prepared by adding the APTT measurement reagent to the blood specimen. In addition, in step S118, the controller 24 controls the sample preparation part 23 to add the calcium solution to the fourth sample after the fourth waiting time has elapsed from the adding of the APTT measurement reagent. In step S119, the controller 24 performs the same processing as that in step S103 such that measurement data of the fourth sample (fourth measurement data) is obtained from the fourth sample to which the calcium solution has been added in step S118.

Figure 13B:
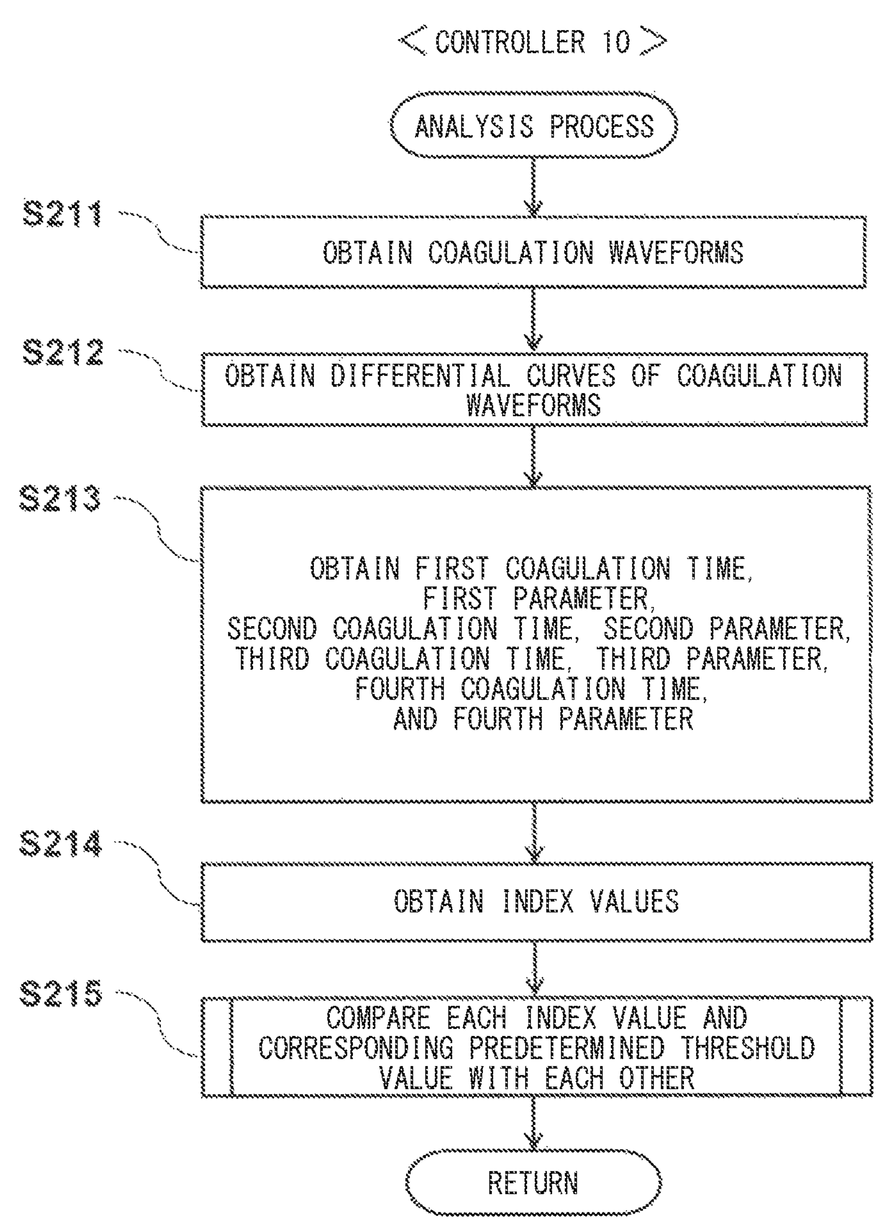
FIG. 13B is a flowchart showing an analysis process to be performed by the controller 10.

With reference to FIG. 13B, an analysis process in the above modification will be described. In step S211, the controller 10 performs the same processing as that in step S201 such that coagulation waveforms of the respective first, second, third, and fourth samples are obtained and normalized. In step S212, the controller 10 differentiates each of the coagulation waveforms to obtain a first-order differential curve, and differentiates the first-order differential curve to obtain a second-order differential curve. Normalization of the coagulation waveforms in step S211 may be omitted. In this case, the controller 10 obtains a first-order differential curve and a second-order differential curve from each of the coagulation waveforms not having been normalized. In step S213, the controller 10 performs the same processing as that in step S203 such that: the first coagulation time and the first parameter are obtained for the first sample; the second coagulation time and the second parameter are obtained for the second sample; the third coagulation time and a third parameter regarding either of the differentials of a third coagulation waveform (hereinafter, referred to as "third parameter") are obtained for the third sample; and the fourth coagulation time and a fourth parameter regarding either of the differentials of a fourth coagulation waveform (hereinafter, referred to as "fourth parameter") are obtained for the fourth sample. The third coagulation time and the third parameter are a coagulation time and a parameter regarding either of the differentials of the corresponding coagulation waveform which have been obtained on the basis of the third measurement data of the third sample. The fourth coagulation time and the fourth parameter are a coagulation time and a parameter regarding either of the differentials of the corresponding coagulation waveform which have been obtained on the basis of the fourth measurement data of the fourth sample.

In step S214, the controller 10 obtains, through an arithmetic operation, a first index value and a fifth index value which are based on the coagulation times and/or the parameters obtained in step S213. The first index value can be, for example, a value calculated by using any of the above mathematical expressions 1 to 8. The fifth index value can be, for example, a value calculated by using any of the following mathematical expressions 9 to 16. In the mathematical expressions, "−" indicates subtraction, and "/" indicates division.

(Index value 5)=(third coagulation time)−(fourth coagulation time) (mathematical expression 9)

(Index value 5')=(fourth coagulation time)−(third coagulation time) (mathematical expression 10)

(Index value 6)=(third coagulation time)/(fourth coagulation time) (mathematical expression 11)

(Index value 6')=(fourth coagulation time)/(third coagulation time) (mathematical expression 12)

(Index value 7)=(value of third parameter)−(value of fourth parameter) (mathematical expression 13)

(Index value 7')=(value of fourth parameter)−(value of third parameter) (mathematical expression 14)

(Index value 8)=(value of third parameter)/(value of fourth parameter) (mathematical expression 15)

(Index value 8')=(value of fourth parameter)/(value of third parameter) (mathematical expression 16)

The first and fifth index values are not limited to the values calculated by using mathematical expressions exemplified by the mathematical expressions 1 to 16. Modifications of the index values have been described above. In a preferred embodiment, the first index value is a value calculated by using the mathematical expression 1 or 3, and the fifth index value is a value calculated by using the mathematical expression 11 or 15.

In step S215, the controller 10 compares each of the first and fifth index values and a predetermined threshold value corresponding to the index value with each other. With reference to FIG. 14, a comparison process in step S215 will be described. FIG. 14 shows a comparison process in a case where: the first index value is a value obtained by subtracting the second coagulation time from the first coagulation time (the value calculated by using the mathematical expression 1); and the fifth index value is the value of the ratio of the third coagulation time to the fourth coagulation time (the value calculated by using the mathematical expression 11).

In step S801, the first index value and the first threshold value are compared with each other, and, in a case where the first index value is lower than the first threshold value (in the case of "NO"), the controller 10 advances the process to step S802 in which the controller 10 determines that the blood specimen is suspected of having a cause of prolongation other than LA and heparin. In step S801, in a case where the first index value is not lower than the first threshold value (in the case of "YES"), the controller 10 advances the process to step S803. In step S803, the fifth index value and a fifth threshold value are compared with each other, and, in a case where the fifth index value is not lower than the fifth threshold value (in the case of "NO"), the controller 10 advances the process to step S804 in which the controller 10 determines that the blood specimen is suspected of containing LA. In step S803, in a case where the fifth index value is lower than the fifth threshold value (in the case of "YES"), the controller 10 advances the process to step S805 in which the controller 10 determines that the blood specimen is suspected of containing heparin. For example, in a case where the third coagulation time is a coagulation time of a sample for which the waiting time is 330 seconds, and the fourth coagulation time is a coagulation time of a sample for which the waiting time is 550 seconds, the fifth threshold value may be 1.

Hereinafter, the present disclosure will be described in further detail using Examples. However, the present disclosure is not limited to these Examples.

EXAMPLES

Example 1

For each of blood specimens having APTTs prolonged owing to various causes, the manner in which the measured APTT thereof was changed when the time for incubation performed after the blood specimen was mixed with an APTT measurement reagent was changed from a time for incubation performed in ordinary APTT measurement, was examined. In addition, whether distinguishment between causes of prolonging the APTTs was possible on the basis of obtained APTTs, was examined.

(1) Reagents and Blood Specimens

Revohem (registered trademark) APTT SLA (Sysmex Corporation) was used as an APTT measurement reagent. This reagent contains ellagic acid and synthetic phospholipid. A 25-mM calcium chloride solution (Sysmex Corporation) was used as a calcium solution. Normal plasmas (33 examples) obtained from healthy individuals, LA-containing plasmas (12 examples) obtained from LA-positive patients, coagulation factor-deficient plasmas (16 examples) obtained from patients deficient in factor VIII or factor IX, heparin-containing plasmas (11 examples) obtained from heparin-administered patients, warfarin-containing plasmas (6 examples) obtained from warfarin-administered patients, and DOAC-containing plasmas (17 examples) obtained from direct oral anticoagulant (DOAC)-administered patients, were used as blood specimens.

(2) Ordinary Measurement of Coagulation Times

Figure 15:
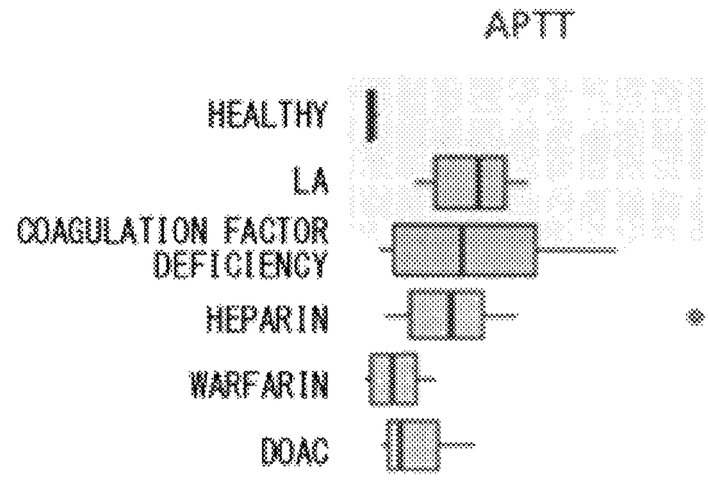
FIG. 15 is a boxplot showing APTTs of respective blood specimens measured at an ordinary incubation time (130 seconds)

Each of the blood specimens (50 μl) was heated at 37° C. for 1 minute. Thereafter, the APTT measurement reagent (50 μl) was added to the blood specimen, and the mixture was incubated at 37° C. for 130 seconds. Then, the calcium solution (50 μl) was added to the mixture of the blood specimen and the APTT measurement reagent, measurement data of transmitted light intensity at a wavelength of 660 nm was obtained for the blood specimen, and a coagulation time was obtained from the obtained measurement data. Therefore, the waiting time from the adding of the APTT measurement reagent to the adding of the calcium solution was 130 seconds. All of these operations were performed with a fully automatic coagulation time measurement apparatus CS-5100 (Sysmex Corporation). The APTTs of the respective blood specimens have been indicated with a boxplot in FIG. 15. As seen from FIG. 15, the coagulation times of the blood specimens other than the normal plasmas were prolonged. However, distinguishment between the causes of prolonging the coagulation times of the blood specimens other than the normal plasmas was difficult with only the APTTs.

(3) Measurement of Coagulation Times with Waiting Time being Changed

Figure 16:
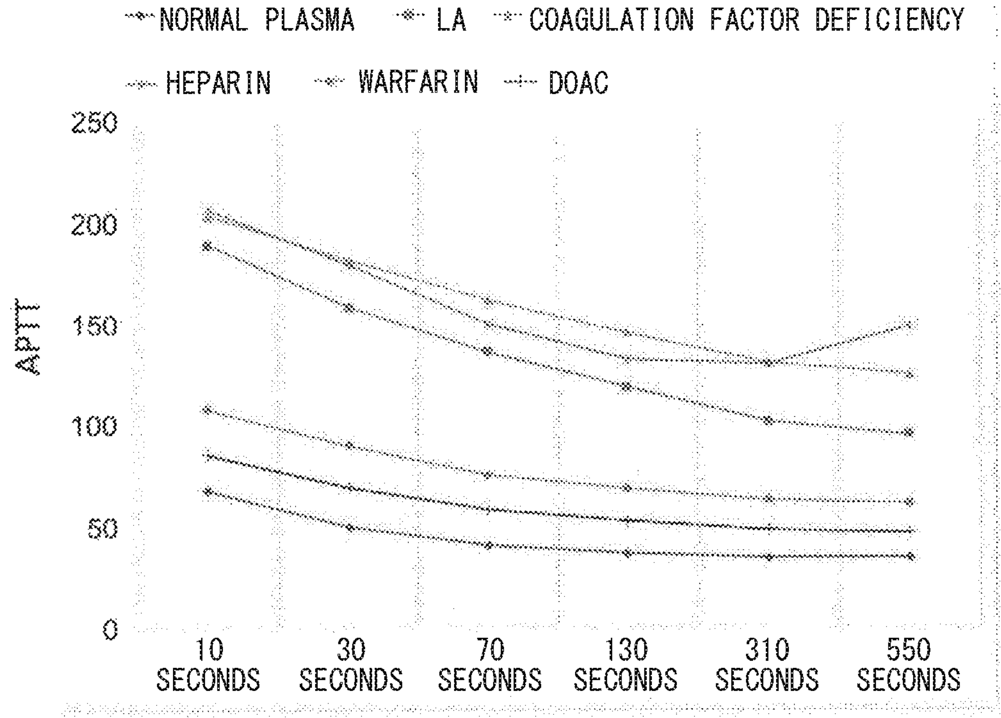
FIG. 16 is a graph showing APTTs, at respective waiting times, of normal plasmas, LA-containing blood specimens, coagulation factor-deficient blood specimens, heparin-containing blood specimens, warfarin-containing blood specimens, and DOAC-containing blood specimens.

Each of the blood specimens (50 μl) was heated at 37° C. for 1 minute. Thereafter, the APTT measurement reagents (50 μl) were added to the blood specimens, and the mixtures were incubated at 37° C. for 10 seconds, 30 seconds, 70 seconds, 130 seconds, 310 seconds, and 550 seconds. Then, coagulation times of the blood specimens were obtained in the same manner as in the above measurement (2). Therefore, the waiting times from the adding of the APTT measurement reagent to the adding of the calcium solution were 10 seconds, 30 seconds, 70 seconds, 130 seconds, 310 seconds, and 550 seconds. All of these operations were performed with CS-5100. FIG. 16 is a graph showing APTTs, at the respective waiting times, of the normal plasma, the LA-containing blood specimen, the coagulation factor-deficient blood specimen, the heparin-containing blood specimen, the warfarin-containing blood specimen, and the DOAC-containing blood specimen. As shown in FIG. 16, with the waiting time being shorter than 130 seconds, the APTTs of all of the blood specimens tended to be elongated, and the APTTs of the LA-containing blood specimen, the coagulation factor-deficient blood specimen, and the heparin-containing blood specimen tended to be elongated more than the APTTs of the normal plasma, the warfarin-containing blood specimen, and the DOAC-containing blood specimen. Meanwhile, with the waiting time being longer than 130 seconds, the APTTs of the normal plasma, the LA-containing blood specimen, the coagulation factor-deficient blood specimen, the DOAC-containing blood specimen, and the warfarin-containing blood specimen tended to be shortened, but the APTTs of the heparin-containing blood specimen tended to be elongated.

(4) Obtainment of Index Values Based on Coagulation Times

Index values each based on APTTs at two different waiting times were obtained for each of the blood specimens in order to quantitatively evaluate a change, in APTT, that occurred according to the change in waiting time. Specifically, the value of the difference ([first APTT]−[second APTT]) between an APTT (first APTT) at a waiting time of 10 seconds and an APTT (second APTT) at a waiting time of 30 seconds, was calculated. In addition, the value of the ratio ([third APTT]/[fourth APTT]) of an APTT (third APTT) at a waiting time of 310 seconds to an APTT (fourth APTT) at a waiting time of 550 seconds, was calculated. The values calculated for each of the blood specimens have been indicated with boxplots in FIG. 17A and FIG. 17B.

Figures 17A, 17B:
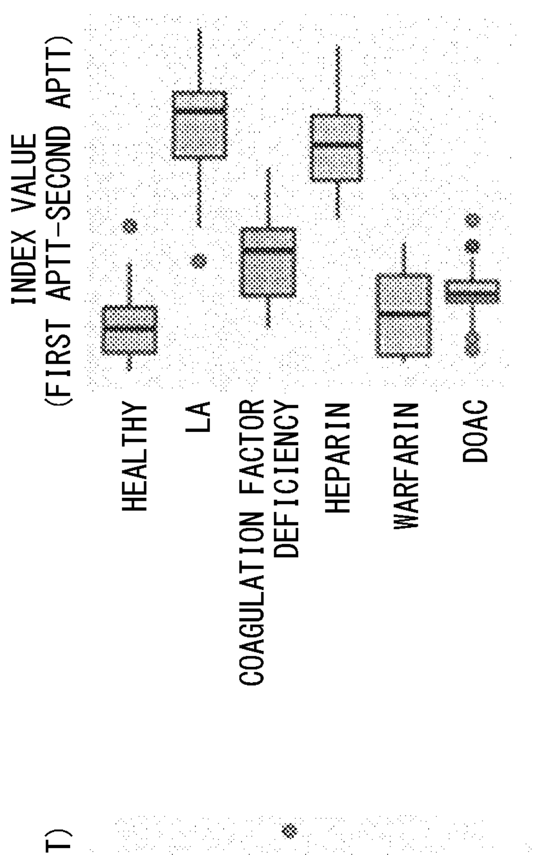
FIG. 17A is a boxplot showing the value of the difference between coagulation times calculated for each of the blood specimens.
FIG. 17B is a boxplot showing the value of the ratio between coagulation times calculated for each of the blood specimens.

As shown in FIG. 17A, the difference between the first APTT and the second APTT took a high value for each of the LA-containing plasma and the heparin-containing plasma. This result has indicated that whether the blood specimen is suspected of containing either of LA and heparin or is suspected of having a cause other than LA and heparin (coagulation factor deficiency, warfarin, or DOAC), can be determined on the basis of the value of the difference between the first APTT and the second APTT. Meanwhile, as shown in FIG. 17B, the ratio of the third APTT to the fourth APTT took a low value for the heparin-containing plasma. This result has indicated that whether the blood specimen is suspected of containing heparin or is suspected of having a cause other than heparin (LA, coagulation factor deficiency, warfarin, or DOAC), can be determined on the basis of the value of the ratio of the third APTT to the fourth APTT. Further, it has been indicated that use of the value of the difference between the first APTT and the second APTT and the value of the ratio of the third APTT to the fourth APTT makes it possible to determine whether the blood specimen is suspected of containing LA, is suspected of containing heparin, or is suspected of having a cause other than LA and heparin.

Example 2

Whether distinguishment between the causes of prolonging the APTTs was possible also on the basis of parameters regarding differentials of coagulation waveforms obtained through coagulation time measurement with the waiting time being changed, was examined.

(1) Obtainment of Index Values Based on Parameters Regarding Differentials of Coagulation Waveforms Coagulation waveforms and first-order differential curves differentiated therefrom were obtained from time-series datasets regarding each of the blood specimens obtained in Example 1. From each of the first-order differential curves, a maximum coagulation speed (|min 1|) was obtained as a parameter regarding the differential of the corresponding coagulation waveform. The value of the difference ([first |min 1|]−[second |min 1|]) between |min 1| (first |min 1|) at a waiting time of 10 seconds and |min 1| (second |min 1|) at a waiting time of 30 seconds was calculated in the same manner as in Example 1. In addition, the value of the ratio ([third |min 1|]–[fourth |min 1|]) of |min 1| (third |min 1|) at a waiting time of 310 seconds to |min 1| (fourth |min 1|) at a waiting time of 550 seconds was calculated. The values calculated for each of the blood specimens have been indicated with boxplots in FIG. 18A and FIG. 18B.

Figures 18A, 18B:
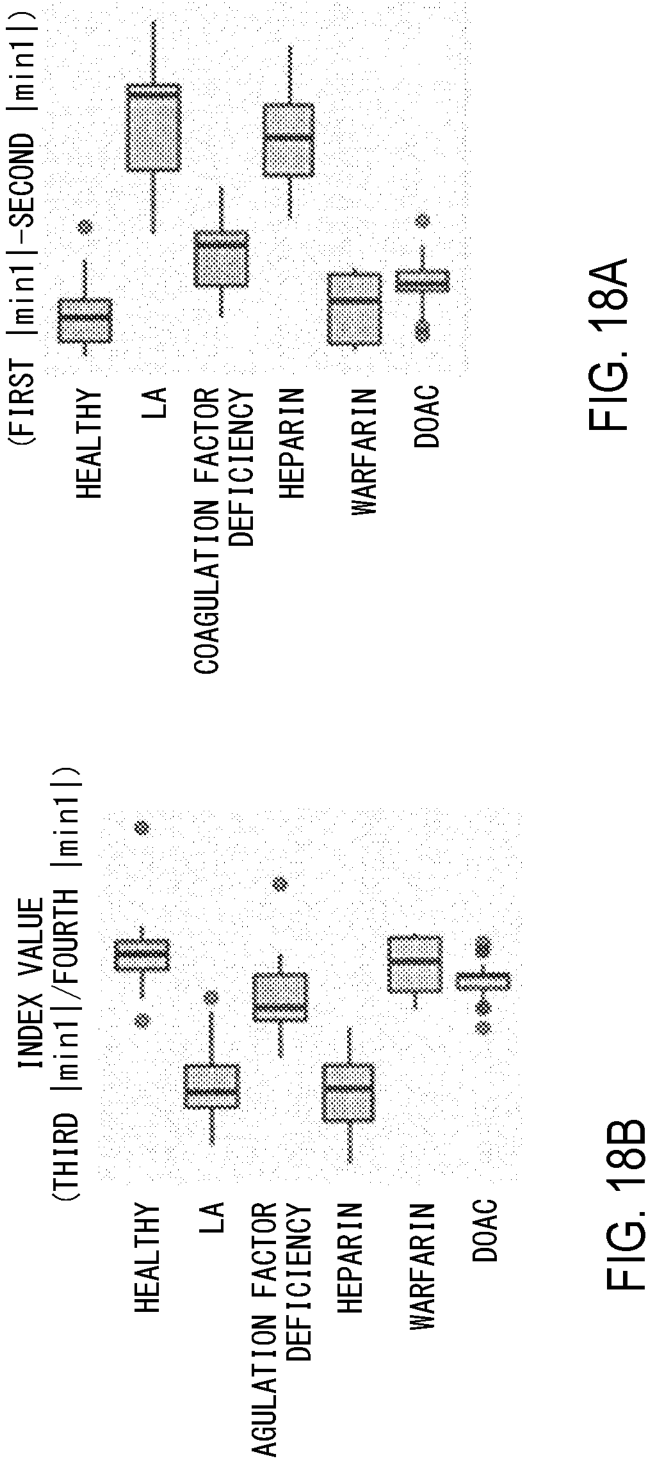
FIG. 18A is a boxplot showing the value of the difference between parameters, regarding differentials of coagulation waveforms, calculated for each of the blood specimens.
FIG. 18B is a boxplot showing the value of the ratio between parameters, regarding differentials of coagulation waveforms, calculated for each of the blood specimens.

As shown in FIG. 18A, the difference between the first |min 1| and the second |min 1| took a high value for each of the LA-containing plasma and the heparin-containing plasma. Meanwhile, as shown in FIG. 18B, the ratio of the third |min 1| to the fourth |min 1| took a low value for each of the LA-containing plasma and the heparin-containing plasma. These results have indicated that whether the blood specimen is suspected of containing either of LA and heparin or is suspected of having a cause other than LA and heparin (coagulation factor deficiency, warfarin, or DOAC), can be determined on the basis of the value of the difference between the first |min 1| and the second |min 1| or the value of the ratio of the third |min 1| to the fourth |min 1|.

What is claimed is:

1. An analysis system configured to analyze a blood sample obtained from a single patient and determine a suspected cause of prolongation of time to form coagulation in the blood sample, wherein the suspected cause relates to possible presence of lupus anticoagulant (LA) in the blood sample, possible presence of heparin in the blood sample or suspicion of another cause other than the presence of LA and heparin, the analysis system comprising:

a sample preparator including a sample dispenser including a first arm and a first pipette attached to the first arm, the sample dispenser configured to dispense the blood sample in each of a first cuvette and a second cuvette, and a reagent dispenser including a second arm and a second pipette attached to the second arm, the reagent dispenser configured to dispense an activated partial thromboplastin time (APTT) measurement reagent and a calcium solution in each of the first cuvette and the second cuvette;

a light applicator configured to apply light to the first cuvette and the second cuvette;

a detector configured to detect the light through the first cuvette and the second cuvette; and a controller operably connected with the sample preparator, the light applicator, and the detector, wherein the controller is programmed to:

control the sample preparator to dispense the blood sample from the single patient and the APTT measurement reagent in the first cuvette, and dispense the calcium solution in the first cuvette a first waiting time after dispensing the blood sample and the APTT measurement reagent in the first cuvette, and dispense the blood sample from the single patient and the APTT measurement reagent in the second cuvette, and dispense the calcium solution in the second cuvette a second waiting time after dispensing the blood sample and the APTT measurement reagent in the second cuvette, wherein the second waiting time is set to longer than the first waiting time, and neither the first cuvette nor the second cuvette contains other blood sample than the blood sample from the single patient, control the light applicator to apply light to the first cuvette and the second cuvette that each contain the blood sample, the APTT measurement reagent, and the calcium solution, obtain from the detector a first set of coagulation data representing a first light-absorbance profile of the light detected through the first cuvette, obtain from the detector a second set of coagulation data representing a second light-absorbance profile of the light detected through the second cuvette, obtain at least one pair of parameters selected from two pairs of parameters defined below:

(i) a pair of parameters A1 and A2, wherein the parameter A1 relates to a first coagulation time determined from the first light-absorbance profile, and the parameter A2 relates to a second coagulation time determined from the second light-absorbance profile; and (ii) a pair of parameters B1 and B2, wherein the parameter B1 relates a first maximum coagulation speed determined from a first order differentiation of the first light-absorbance profile, and the parameter B2 relates to a second maximum coagulation speed determined from a first order differentiation of the second light-absorbance profile, calculate an arithmetic relationship between the parameters in the selected at least one pair, wherein the calculated arithmetic relationship relates to either a difference between the selected at least one pair of parameters or a ratio between the selected at least one pair of parameters, and analyze the calculated arithmetic relationship relative to at least one predetermined value to determine the suspected cause of prolongation of coagulation time.

2. The analysis system of claim 1, further comprising a heater configured to incubate the blood sample in the first cuvette and the blood sample in the second cuvette, wherein the controller is operably connected to the heater and programmed to control the heater to maintain the blood sample in the first cuvette at a predetermined temperature during the first waiting time, and control the heater to maintain the blood sample in the second cuvette at the predetermined temperature during the second waiting time.

3. The analysis system of claim 1, wherein each of the first waiting time and the second waiting time is set within a range of not shorter than 10 seconds and shorter than 120 seconds.

4. The analysis system of claim 3, wherein the first waiting time is set to not shorter than 10 seconds and not longer than 20 seconds, and the second waiting time is set to longer than 20 seconds and not longer than 100 seconds, wherein the second waiting time is set to be longer than the first waiting time by at least 5 seconds.

5. The analysis system of claim 1, wherein each of the first waiting time and the second waiting time is set within a range of longer than 140 seconds and not longer than 600 seconds.

6. The analysis system of claim 5, wherein the first waiting time is set to longer than 150 seconds and not longer than 400 seconds, and the second waiting time is set to be longer than 400 seconds and not longer than 600 seconds, wherein the second waiting time is set to be longer than the first waiting time by at least 30 seconds.

7. The analysis system of claim 1, wherein the controller is programmed to report the calculated arithmetic relationship as information on the suspected cause for prolonged coagulation time.

8. The analysis system of claim 1, wherein the sample dispenser is configured to dispense the blood sample in each of a third cuvette and a fourth cuvette, the reagent dispenser is configured to dispense the APTT measurement reagent and the calcium solution in each of the third cuvette and the fourth cuvette, the light applicator is configured to apply the light to the third cuvette and the fourth cuvette, the detector is configured to detect the light from the light applicator that has passed through the third cuvette and the fourth cuvette, and the controller is programmed to:

control the sample preparator to dispense the blood sample and the APTT measurement reagent in the third cuvette, and dispense the calcium solution in the third cuvette a third waiting time after dispensing the blood sample and the APTT measurement reagent in the third cuvette, wherein the third waiting time is set to longer than the second waiting time, and dispense the blood sample and the APTT measurement reagent in the fourth cuvette, and dispense the calcium solution in the fourth cuvette a fourth waiting time after dispensing the blood sample and the APTT measurement reagent in the fourth cuvette, wherein the fourth waiting time is set to longer than the third waiting time, and neither the third cuvette nor the fourth cuvette contains other blood sample than the blood sample from the single patient, control the light applicator to apply the light to the third cuvette and the fourth cuvette that each contain the blood sample, the APTT measurement reagent, and the calcium solution, obtain from the detector a third set of coagulation data representing a third light-absorbance profile of the light detected through the third cuvette, obtain from the detector a fourth coagulation data representing a fourth light-absorbance profile of the light detected through the fourth cuvette, and obtain first and second pairs of parameters selected from four pairs of parameters (i), (ii), (iii) and (iv) defined in claim 1 and defined below:

(iii) a pair of parameters A3 and A4, wherein the parameter A3 relates to a third coagulation time determined from the third light-absorbance profile, and the parameter A4 relates to a fourth coagulation time determined from the fourth light-absorbance profile; and (iv) a pair of parameters B3 and B4, wherein the parameter B3 relates a third maximum coagulation speed determined from a first order differentiation of the third light-absorbance profile, and the parameter B4 relates to a fourth maximum coagulation speed determined from a first order differentiation of the fourth light-absorbance profile, wherein the controller is programmed so that calculating an arithmetic relationship between the parameters in the selected at least one pair comprises calculating a first arithmetic relationship of two parameters in the selected first pair and a second arithmetic relationship of two parameters in the selected second pair, and wherein the controller is further programmed so that analyzing the calculated arithmetic relationship relative to at least one predetermined value to determine the suspected cause of prolongation of coagulation time comprises analyzing the first arithmetic relationship relative to a first predetermined value and analyzing the second arithmetic relationship relative to a second predetermined value and evaluating a combination of results of analyzing the first arithmetic relationship relative to the first predetermined value and analyzing the second arithmetic relationship relative to the second predetermined value to determine the suspected cause of prolongation of coagulation time.

9. The analysis system of claim 8, wherein each of the first waiting time and the second waiting time is set within a range of not shorter than 10 seconds and shorter than 120 seconds, and each of the third waiting time and the fourth waiting time is set within a range of longer than 140 seconds and not longer than 600 seconds.

10. The analysis system of claim 9, wherein the first waiting time is set to not shorter than 10 seconds and not longer than 20 seconds, the second waiting time is set to be longer than 20 seconds and not longer than 100 seconds and is longer than the first waiting time by at least 5 seconds, the third waiting time is set to be longer than 150 seconds and not longer than 400 seconds, and the fourth waiting time is set to be longer than 400 seconds and not longer than 600 seconds and is longer than the third waiting time by at least 30 seconds.

11. A method for analyzing a blood sample obtained from a single patient and determining a suspected cause of prolongation of time to form coagulation in the blood sample, wherein the suspected cause relates to possible presence of lupus anticoagulant (LA) in the blood sample, possible presence of heparin in the blood sample or suspicion of another cause other than the presence of LA and heparin, the method comprising:

dispensing the blood sample obtained from the single patient and an activated partial thromboplastin time (APTT) measurement reagent in a first cuvette and dispensing a calcium solution in the first cuvette a first waiting time after dispensing the blood sample and the APTT measurement reagent in the first cuvette;

dispensing the blood sample obtained from the single patient and the APTT measurement reagent in a second cuvette and dispensing the calcium solution in the second cuvette a second waiting time after dispensing the blood sample and the APTT measurement reagent in the second cuvette, wherein the second waiting time is set to longer than the first waiting time, and neither the first cuvette nor the second cuvette contains other blood sample than the blood sample from the single patient;

applying light to the first cuvette and the second cuvette that each contain the blood sample, the APTT measurement reagent and the calcium solution;

detecting the light that has passed through the first cuvette and the second cuvette;

obtaining a first set of coagulation data representing a first light-absorbance profile of the light detected through the first cuvette;

obtaining a second set of coagulation data representing a second light-absorbance profile of the light detected through the second cuvette, obtaining at least one pair of parameters selected from two pairs of parameters defined below:

(i) a pair of parameters A1 and A2, wherein the parameter A1 relates to a first coagulation time determined from the first light-absorbance profile, and the parameter A2 relates to a second coagulation time determined from the second light-absorbance profile; and (ii) a pair of parameters B1 and B2, wherein the parameter B1 relates a first maximum coagulation speed determined from a first order differentiation of the first light-absorbance profile, and the parameter B2 relates to a second maximum coagulation speed determined from a first order differentiation of the second light-absorbance profile;

calculating an arithmetic relationship between the parameters in the selected at least one pair, wherein the calculated arithmetic relationship relates to either a difference between the selected at least one pair of parameters or a ratio between the selected at least one pair of parameters; and analyzing the calculated arithmetic relationship relative to at least one predetermined value to determine the suspected cause of prolongation of coagulation time.

* * * * *